(12) United States Patent
Fuhshuku et al.

(10) Patent No.: US 8,173,608 B2
(45) Date of Patent: May 8, 2012

(54) COMPOUND HAVING CYCLIC STRUCTURE AND USE THEREOF

(75) Inventors: Ken-ichi Fuhshuku, Yokohama (JP); Kenji Mori, Yokohama (JP); Takuya Tashiro, Yokohama (JP); Masaru Taniguchi, Yokohama (JP); Ken-ichiro Seino, Yokohama (JP)

(73) Assignee: Riken, Wako-shi (JP)

( * ) Notice: Subject to any disclaimer, the term of this patent is extended or adjusted under 35 U.S.C. 154(b) by 717 days.

(21) Appl. No.: 11/817,616

(22) PCT Filed: Mar. 3, 2006

(86) PCT No.: PCT/JP2006/304671
§ 371 (c)(1),
(2), (4) Date: Jan. 7, 2009

(87) PCT Pub. No.: WO2006/093352
PCT Pub. Date: Sep. 8, 2006

(65) Prior Publication Data
US 2009/0215707 A1     Aug. 27, 2009

(30) Foreign Application Priority Data
Mar. 4, 2005 (JP) .................................. 2005-059934

(51) Int. Cl.
*A01N 43/04* (2006.01)
*A61K 31/70* (2006.01)
*C07G 3/00* (2006.01)
*C07H 17/02* (2006.01)

(52) U.S. Cl. ................ 514/27; 514/23; 514/25; 536/4.1; 536/17.2; 536/17.3; 536/17.4

(58) Field of Classification Search .......................... None
See application file for complete search history.

(56) References Cited

U.S. PATENT DOCUMENTS
2005/0215767 A1 * 9/2005 Koenig et al. .............. 530/387.2

FOREIGN PATENT DOCUMENTS
| EP | 0 988 860 A1 | 3/2000 |
| WO | WO 03/040097 A1 | 5/2003 |
| WO | WO 03/066065 A1 | 8/2003 |

OTHER PUBLICATIONS

Barrett et al., *J. Org. Chem.*, 55: 5194-5196 (1990).
Barrett et al., *J. Org. Chem.*, 56: 2787-2800 (1991).
Burtoloso et al., *Tetrahedron Letters*, 45: 3355-3358 (2004).
Davis et al., *Tetrahedron*, 60: 5111-5115 (2004).
Herdeis et al., *Eur. J. Org. Chem.*: 1407-1414 (1999).
Hirai et al., *Tetrahedron Letters*, 33(51): 7893-7894 (1992).
Hiraki et al., *Tetrahedron Letters*, 36(27): 4841-4844 (1995).
Yang et al., *Tetrahedron: Asymmetry*, 10: 2311-2318 (1999).

* cited by examiner

*Primary Examiner* — Traviss C McIntosh, III
(74) *Attorney, Agent, or Firm* — Leydig, Voit & Mayer, Ltd.

(57) ABSTRACT

The present invention relates to a compound represented by the following formula (1')

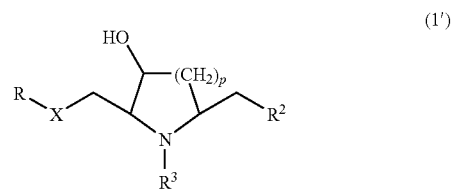

(1')

wherein R is an aldopyranose residue, $R^2$ is a C2-18 hydrocarbon group optionally having substituent(s), $R^3$ is an acyl group, X is an oxygen atom, a sulfur atom or —NH—, and p is an integer of 0-4, or a salt thereof.

The compound of the present invention has a specific immunoregulatory ability, and is useful for the prophylaxis or treatment of autoimmune diseases and the like.

18 Claims, 6 Drawing Sheets

COMPOUND HAVING CYCLIC STRUCTURE AND USE THEREOF

TECHNICAL FIELD

The present invention relates to a compound having a cyclic structure, which is useful for the prophylaxis or treatment of autoimmune diseases and use thereof.

BACKGROUND ART

The immune system distinguishes self from nonself and defends self by excluding nonself from the body. The immune system has a skillful regulatory function to minimize the attack on the self cells (components), and autoimmune diseases are considered to be developed due to collapsed regulatory function. The autoimmune disease is largely divided into systemic autoimmune diseases and organ-specific autoimmune diseases. Of these, the organ-specific autoimmune disease refers to the diseases associated with chronic inflammations in particular organs or tissues (brain, liver, eye, arthrosis) and considered to be caused by an immune response to an autoantigen specific the organ (autoimmune response). Representative diseases include multiple sclerosis (brain, spinal cord) and rheumatoid arthritis (arthrosis). These diseases have many common aspects such as deviation of Th1/Th2 immune balance toward Th1, and the like, even when the disordered organs are different, and the treatment methods are basically the same.

NKT cell, which is one kind of lymphocytes constructing the immune system, has an NK cell receptor and a T-cell receptor, and has been identified as a new lymphocyte group showing different characteristics from those of other lymphocyte series (T, B, NK cells). One of the functions characterizing the NKT cell is that it recognizes, as an antigen, glycolipid (α-galactosylceramide) presented to CD1d belonging to major histocompatibility complex (MHC) class I molecules, thereby abundantly producing cytokines such as IL-4 and the like.

Noting such function of NKT cell, a therapeutic drug for autoimmune diseases comprising α-galactosylceramide as an active ingredient has been proposed (WO 98/044928). Since IL-4 produced by activation of NKT cells shows an autoimmune disease-suppressive action, autoimmune diseases are expected to be treated by activating NKT cells by administration of α-galactosylceramide.

DISCLOSURE OF THE INVENTION

However, the NKT cell activated by the administration of α-galactosylceramide has a problem in that it induces production of IFN-γ that aggravates autoimmune diseases, along with the production of IL-4 that suppresses autoimmune diseases, whereby they can antagonize each other and, as a result, a sufficient treatment effect of autoimmune diseases cannot be afforded.

The present invention has been made in view of such situation and its problem to be solved is provision of a novel compound effective for the prophylaxis or treatment of an autoimmune disease and an intermediate useful for the synthesis of the compound. In addition, the present invention aims at providing a pharmaceutical agent such as an agent for the prophylaxis or treatment of an autoimmune disease, which comprises such novel compound, and the like.

The present inventors have conducted intensive studies in an attempt to solve the above-mentioned problems and found that a compound having a cyclic structure in the sphingosine base moiety of a glycolipid has a specific immunoregulatory ability and is extremely effective for the treatment of an autoimmune disease, which resulted in the completion of the present invention.

Accordingly, the present invention provides the following.

[1] A compound represented by the following formula (1') or a salt thereof (hereinafter to be abbreviated as compound (1')):

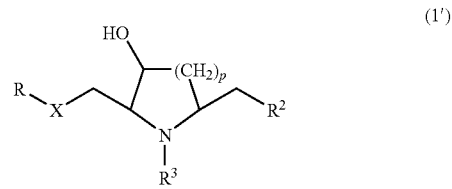

wherein R is an aldopyranose residue, $R^2$ is a C2-18 hydrocarbon group optionally having substituent(s), $R^3$ is an acyl group, X is an oxygen atom, a sulfur atom or —NH—, and p is an integer of 0-4.

[2] A compound represented by the following formula (1) or a salt thereof (hereinafter to be abbreviated as compound (1)):

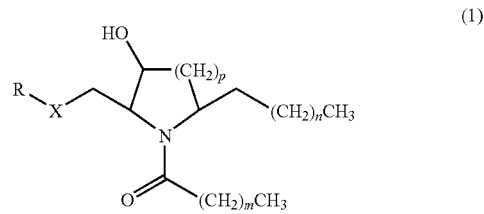

wherein R, X and p are as defined above, m is an integer of 0-26, and n is an integer of 0-16.

[3] The compound of the above-mentioned [1] or [2], wherein R is α-D-galactopyranosyl, or a salt thereof.

[4] A compound represented by the following formula (5') or (7') or a salt thereof (hereinafter to be abbreviated as compound (5') or compound (7'), respectively):

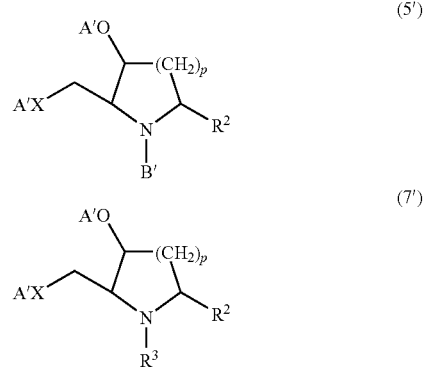

wherein $R^2$, $R^3$, X and p are as defined above, each A' is independently a hydrogen atom or a protecting group, and B' is a hydrogen atom or a protecting group.

[5] An azetidine compound represented by the following formula (2) or a salt thereof (hereinafter to be abbreviated as compound (2)):

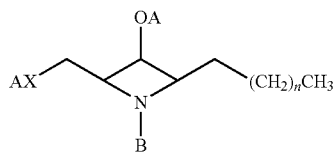

wherein X and n are as defined above, each A is independently a hydrogen atom or a t-butyldimethylsilyl group, and B is a hydrogen atom, a tosyl group or —CO(CH$_2$)$_m$CH$_3$ (m is as defined above).

[6] A pyrrolidine compound represented by the following formula (3) or a salt thereof (hereinafter sometimes to be abbreviated as compound (3)):

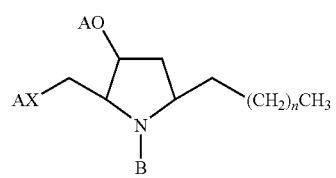

wherein each symbol is as defined above.

[7] A pharmaceutical agent comprising the compound of any of the above-mentioned [1]-[3] or a salt thereof.

[8] An agent for the prophylaxis or treatment of an autoimmune disease, comprising the compound of any of the above-mentioned [1]-[3] or a salt thereof.

[9] An NKT cell activator comprising the compound of any of the above-mentioned [1]-[3] or a salt thereof.

[10] A selective IL-4 production inducing agent comprising the compound of any of the above-mentioned [1]-[3] or a salt thereof.

[11] An agent for the prophylaxis or treatment of a disease caused by hyperfunction of Th1 cell, which comprises the compound of any of the above-mentioned [1]-[3] or a salt thereof.

[12] A method of producing a compound represented by the following formula (B) or a salt thereof (hereinafter to be abbreviated as compound (B)), which comprises cyclizing a compound represented by the following formula (A) or a salt thereof (hereinafter to be abbreviated as compound (A)).

[13] A method of producing a compound represented by the following formula (C) or a salt thereof (hereinafter to be abbreviated as compound (C)), which comprises removing an N atom-protecting group in cyclic amine of compound (B).

[14] A method of producing a compound represented by the following formula (D) or a salt thereof (hereinafter to be abbreviated as compound (D)), which comprises acylating an N atom of cyclic amine of compound (C).

[15] A method of producing a compound represented by the following formula (E) or a salt thereof (hereinafter to be abbreviated as compound (E)), which comprises removing a —XH-protecting group in —CH$_2$XH at the 2-position of cyclic amine of compound (D).

[16] A method of producing a compound represented by the following formula (F) or a salt thereof (hereinafter to be abbreviated as compound (F)), which comprises derivatizing compound (E) into aldopyranosyl and removing a hydroxyl-protecting group at the 3-position of cyclic amine.

[17] A method of producing compound (1'), which comprises removing a hydroxyl-protecting group of aldopyranose of compound (F).

[18] A method of producing compound (1'), which comprises cyclizing compound (A) to give compound (B), removing an N atom-protecting group in cyclic amine of the compound (B) to give compound (C), acylating an N atom of cyclic amine of the compound (C) to give compound (D), removing a —XH-protecting group of —CH$_2$XH at the 2-position of cyclic amine of the compound (D) to give compound (E), derivatizing the compound (E) into aldopyranosyl and removing a hydroxyl-protecting group at the 3-position of cyclic amine to give compound (F), and removing a hydroxyl-protecting group of aldopyranose of the compound (F):

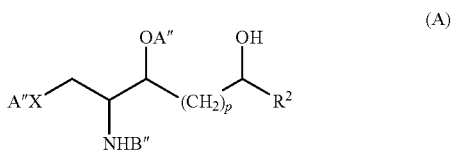

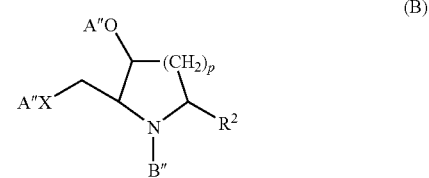

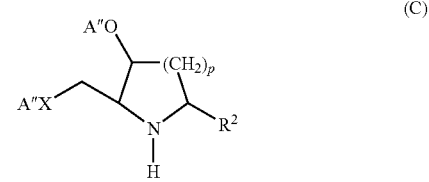

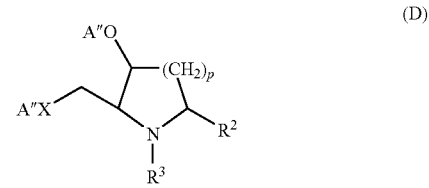

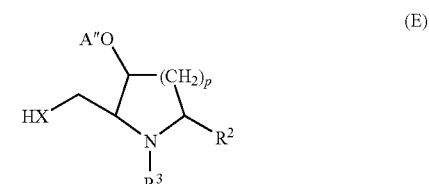

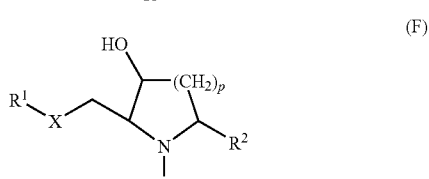

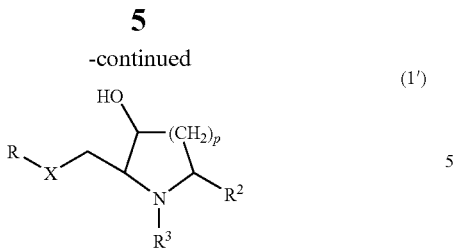

(1')

wherein R, $R^2$, $R^3$ and p are as defined above, $R^1$ is an aldopyranose residue wherein a hydroxyl group is protected, each A" is independently a protecting group, and B" is a protecting group.

[19] A method of producing a compound represented by the following formula (5) or a salt thereof (hereinafter to be abbreviated as compound (5)), which comprises cyclizing a compound represented by the following formula (4) or a salt thereof (hereinafter to be abbreviated as compound (4)).

[20] A method of producing a compound represented by the following formula (6) or a salt thereof (hereinafter to be abbreviated as compound (6)), which comprises detosylating compound (5).

[21] A method of producing a compound represented by the following formula (7) or a salt thereof (hereinafter to be abbreviated as compound (7)), which comprises acylating an N atom of cyclic amine of compound (6)

[22] A method of producing a compound represented by the following formula (8) or a salt thereof (hereinafter to be abbreviated as compound (8)), which comprises removing a t-butyldimethylsilyl group of —$CH_2OH$ at the 2-position of cyclic amine of compound (7).

[23] A method of producing a compound represented by the following formula (9) or a salt thereof (hereinafter to be abbreviated as compound (9)), which comprises derivatizing compound (8) into aldopyranosyl and removing a t-butyldimethylsilyl group of a hydroxyl group at the 3-position of cyclic amine.

[24] A method of producing a compound represented by the following formula (1a) or a salt thereof (hereinafter to be abbreviated as compound (1a)), which comprises removing a hydroxyl-protecting group of aldopyranose of compound (9).

[25] A method of producing compound (1a), which comprises cyclizing compound (4) to give compound (5), subjecting compound (5) to detosylation to give compound (6), acylating N atom of cyclic amine of the compound (6) to give compound (7), removing a t-butyldimethylsilyl group of —$CH_2OH$ at the 2-position of cyclic amine of the compound (7) to give compound (8), derivatizing the compound (8) into aldopyranosyl and removing a t-butyldimethylsilyl group of a hydroxyl group at the 3-position of cyclic amine to give compound (9), and removing a hydroxyl-protecting group of aldopyranose of the compound (9):

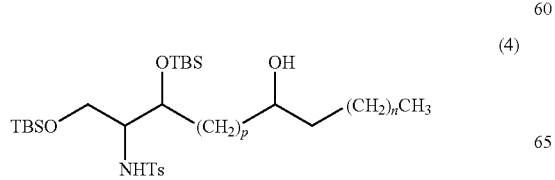

(4)

(5)

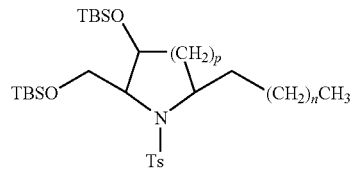

(6)

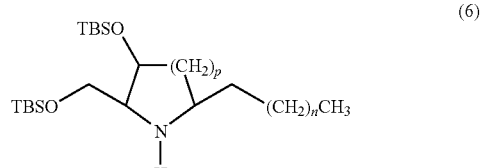

(7)

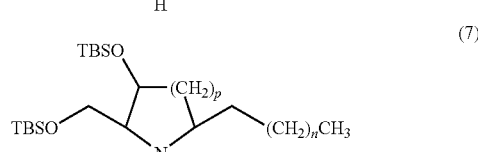

(8)

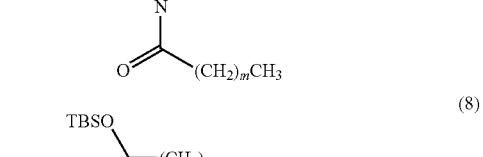

(9)

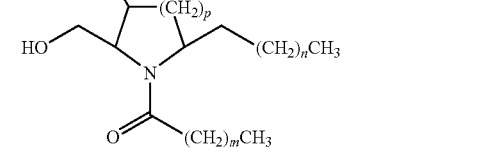

(1a)

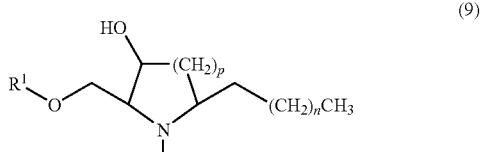

wherein R, $R^1$, m, n and p are as defined above, TBS is a t-butyldimethylsilyl group, and Ts is a tosyl group.

[26] A method of producing a compound represented by the following formula (H) (hereinafter to be abbreviated as compound (H)), which comprises opening the ring of an epoxy group of a compound represented by the following formula (G) (hereinafter to be abbreviated as compound (G)):

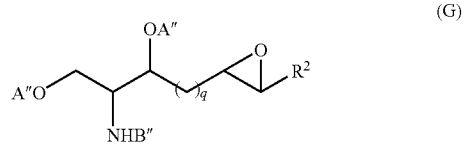

(G)

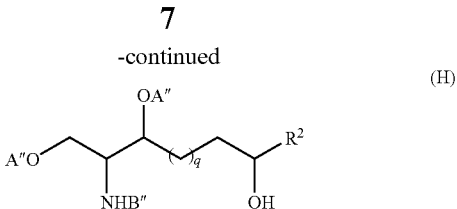

wherein $R^2$, A" and B" are as defined above, and q is an integer of 0-3.

[27] A method of producing a compound represented by the following formula (11) (hereinafter to be abbreviated as compound (11)), which comprises opening the ring of an epoxy group of a compound represented by the following formula (10) (hereinafter to be abbreviated as compound (10)):

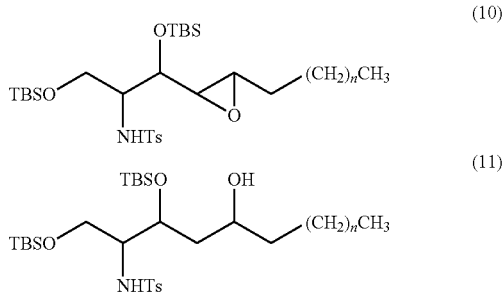

wherein each symbol is as defined above.

BEST MODE FOR EMBODYING THE INVENTION

Figure 1:
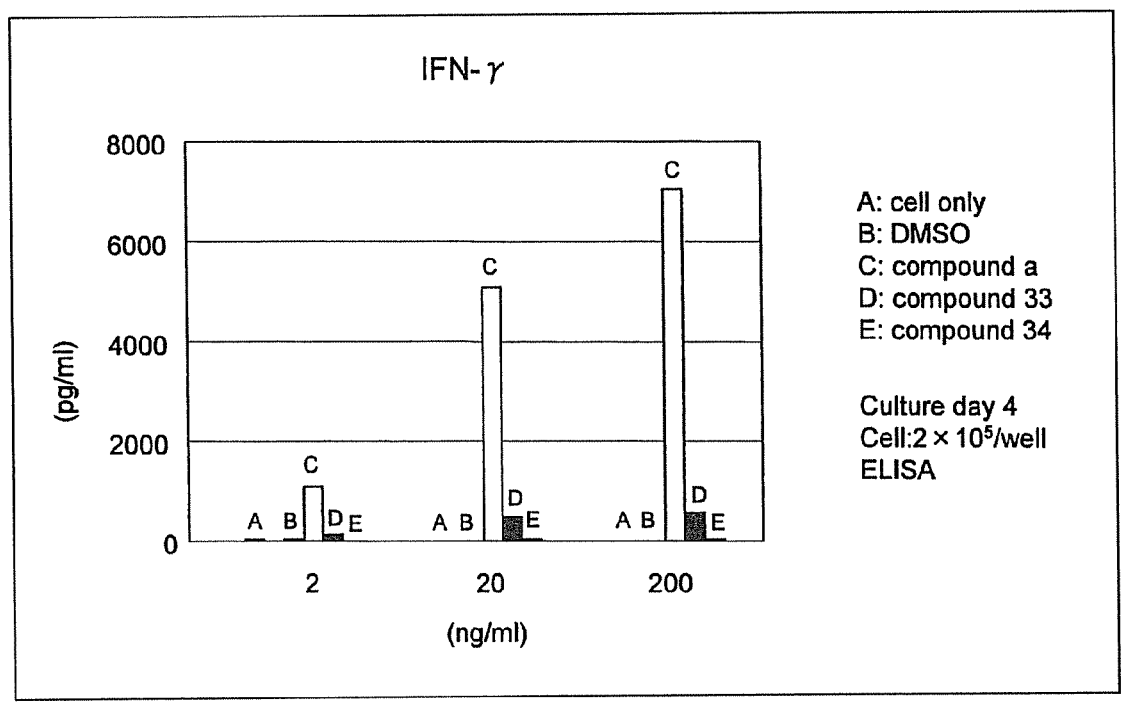
FIG. 1 shows the measurement results of the IFN-γ production amount by sandwich ELISA assay in Experimental Example 1.

The present invention is explained in detail in the following.

First, in the present invention, the definitions of the symbols in the above-mentioned respective formulas are as follows.

R is an aldopyranose residue, and $R^1$ is an aldopyranose residue wherein a hydroxyl group is protected. Here, the aldopyranose residue means a residue excluding a reducing terminal hydroxyl group of aldopyranose. As the aldopyranose residue, for example, α-D-galactopyranosyl, α-D-glucopyranosyl, β-D-galactopyranosyl, β-D-glucopyranosyl and the like can be mentioned. Of these, α-D-galactopyranosyl is preferable from the aspect of pharmacological effect.

As the hydroxyl-protecting group of an aldopyranose residue, acyl group, t-butyldimethylsilyl (TBS) group, benzyl (Bn) group, p-methoxybenzyl (PMB) group and the like can be mentioned. Here, the acyl group as a hydroxyl-protecting group means formyl group; straight chain or branched C1-12 or cyclic C3-10 alkyl-carbonyl group (e.g., acetyl group, propionyl group, butyryl group, isobutyryl group, valeryl group, pivaloyl group, hexanoyl group, acryloyl group, methacryloyl group); or C6-14 aryl-carbonyl group (e.g., benzoyl group, naphthoyl group). The aryl group is a monocyclic-tricyclic aromatic hydrocarbon group and, for example, phenyl group, naphthyl group, anthryl group and phenanthryl group can be mentioned. As the acyl group, acetyl group and benzoyl group are preferable.

As the hydroxyl-protecting group of an aldopyranose residue, benzyl (Bn) group and p-methoxybenzyl (PMB) group are preferable.

$R^2$ is a C2-18 hydrocarbon group optionally having substituent(s). In the present invention, hydrocarbon group is a concept encompassing aliphatic hydrocarbon group and aromatic hydrocarbon group, which may be linear, branched or cyclic and saturated hydrocarbon group or unsaturated hydrocarbon group, and may have an unsaturated bond either at an internal position of a molecule and terminal. As the aliphatic hydrocarbon group, C2-18 (preferably 6-14, more preferably 12-14) alkyl group (e.g., ethyl group, n-propyl group, isopropyl group, n-butyl group, isobutyl group, sec-butyl group, tert-butyl group, n-pentyl group, n-hexyl group, n-heptyl group, n-octyl group, n-nonyl group, n-decyl group, n-undecyl group, n-dodecyl group, tridecyl group, tetradecyl group, pentadecyl group, hexadecyl group, heptadecyl group, octadecyl group, cyclopentyl group, cyclohexyl group); C2-18 (preferably 6-14, more preferably 12-14) alkenyl group (e.g., vinyl group, propenyl group, butenyl group); C2-18 (preferably 6-14, more preferably 12-14) alkynyl group (e.g., ethynyl group, propargyl group, 1-pentynyl group), C3-10 (preferably 5 or 6) cycloalkyl group (e.g., cyclopentyl group, cyclohexyl group); C3-10 (preferably 5 or 6) cycloalkenyl group (e.g., cyclopentenyl group, cyclohexenyl group) and the like can be mentioned. As the aromatic hydrocarbon group, for example, C6-14 aryl group (e.g., phenyl group, naphthyl group) can be mentioned.

In addition, as the substituent of the hydrocarbon group, halogen (preferably, chlorine atom or fluorine atom), alkyl group (preferably C1-10, more preferably C1-4) such as methyl group, ethyl group, propyl group, isopropyl group, butyl group, tert-butyl group and the like; halogen (preferably, chlorine atom or fluorine atom)-substituted alkyl group (as defined for the above-mentioned alkyl group); alkenyl group (preferably C2-6, more preferably C2-4) such as vinyl group, propenyl group and the like; alkynyl group (preferably C2-6, more preferably C2-4) such as ethynyl group, propargyl group and the like; phenyl group; alkoxy group (preferably C1-10, more preferably C1-4) such as methoxy group, ethoxy group, propoxy group, isopropoxy group, butoxy group, tert-butoxy group and the like; aryloxy group such as phenoxy group and the like (preferably C6-14); hydroxyl group; amino group; alkyl(as defined for the above-mentioned alkyl group)amino group such as methylamino group, dimethylamino group, ethylamino group, diethylamino group and the like; and the like can be mentioned. Of these, as the substituent, alkyl group and hydroxyl group are preferable.

As $R^2$, substituted or unsubstituted C2-18 (preferably 6-14) alkyl group is preferable, and alkyl group represented by $-CH_2(CH_2)_nCH_3$ (n is an integer of 0-16) is more preferable.

The acyl group for $R^3$ is an acyl group derived from saturated or unsaturated fatty acid. As the fatty acid, C2-36 (preferably 2-28) saturated or unsaturated fatty acid is preferable, and saturated fatty acid represented by the formula $CH_3(CH_2)_mCOOH$ (m is an integer of 0-26, preferably 14-26) is more preferable. Specifically, palmitic acid, stearic acid, arachidic acid, cerotic acid and the like can be mentioned, with preference given to cerotic acid.

A' is a hydrogen atom or a protecting group. The protecting group for A' means a group for protecting a group represented by HO or HX. That is, when A'X is represented by A'O, it means a hydroxyl-protecting group, when A'X is represented by A'S, it means a mercapto-protecting group, and when A'X is represented by A'HN, it means an amino-protecting group. As the hydroxyl-protecting group and mercapto-protecting group, those similar to the hydroxyl-protecting group recited for $R^1$ can be mentioned. As the amino-protecting group, those similar to the acyl group recited for $R^1$, tosyl (Ts) group, t-butoxycarbonyl group (Boc group), benzyloxycarbonyl group (Cbz group), 9-fluorenylmethoxycarbonyl group (Fmoc group), ethoxycarbonyl group, methoxycarbonyl group, benzyl group and the like can be mentioned. A' is preferably the below-mentioned A, wherein when two A's are present in one molecule, they may be the same or different. In addition, A" is a protecting group defined for the protecting group for A'.

B' is a hydrogen atom or a protecting group. The protecting group for B' means a group for protecting N atom in cyclic amine of compound (5'), and those similar to the amino-protecting group recited for A' can be mentioned. B' is preferably the below-mentioned B. B" is a protecting group defined for the protecting group for B'.

A is a hydrogen atom or a t-butyldimethylsilyl (TBS) group, and B is a hydrogen atom, a tosyl (Ts) group or $-CO(CH_2)_mCH_3$.

X is an oxygen atom, a sulfur atom or $-NH-$, and an oxygen atom is preferable.

m is an integer of 0-26, preferably 14-26. n is an integer of 0-16, preferably 4-12, more preferably 10-12. p is an integer of 0-4, preferably 0-2, and q is an integer of 0-3, preferably 0 or 1.

While compound (1) and compound (1') contain structural isomers of an α form and a β form due to the aldopyranose residue, they may be in any form of an α form, a β form and a mixture thereof. From the aspect of pharmacological effect, an α form is preferable. While compound (1) and compound (1') contain 8 kinds of optical isomers due to the asymmetric carbon atom on cyclic amine, in the present invention, they may be a single optical isomer, or a mixture of two or more kinds of optical isomers at any ratio (including racemates). In the present invention, $-CH_2XR$ is preferably present at the upper side of the cyclic amine, the hydroxyl group and $R^2$ ($-CH_2(CH_2)_nCH_3$ in compound (1)) are preferably present at the lower side of the cyclic amine. Such preferable steric configuration is the same as in the synthetic intermediates for compound (1) and compound (1').

As compound (1'), compound (1) is preferable, and as compound (1), a compound represented by the following formula (12)-(15), (23), (24), (33) or (34) is preferable. Of these, a compound represented by the following formula (12), (14), (23) or (33) is more preferable.

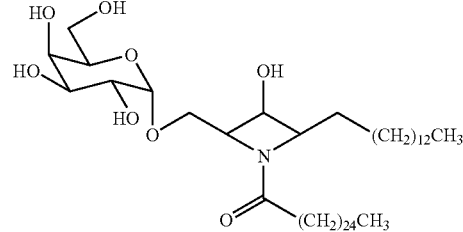

(12)

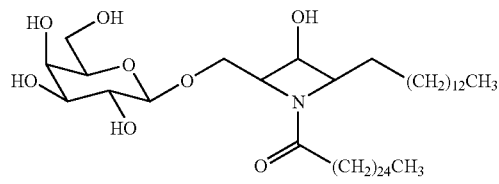

(13)

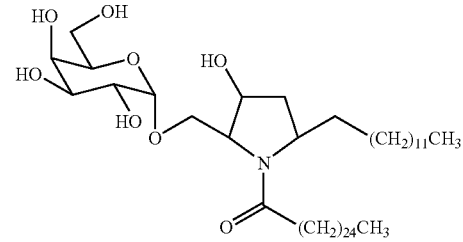

(14)

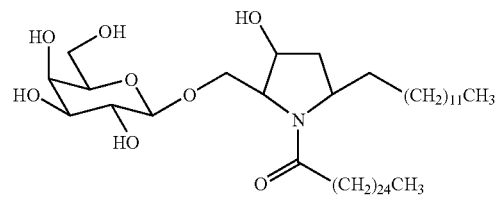

(15)

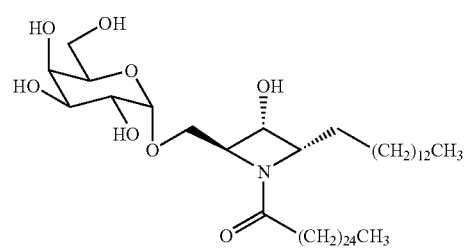

(23)

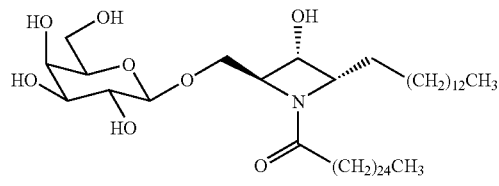

(24)

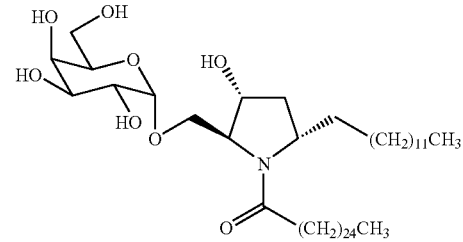

(33)

-continued

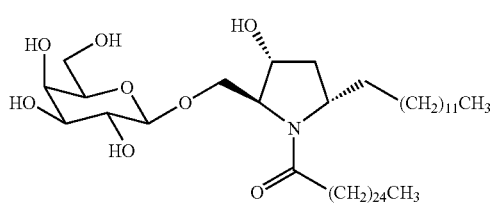

(34)

The salt of compound (1) is preferably a pharmacologically acceptable salt and, for example, inorganic acid salt such as hydrochloride, hydrobromide, hydroiodide, sulfate, nitrate, phosphate and the like; organic acid salt such as succinate, fumarate, acetate, methanesulfonate, toluenesulfonate and the like; alkali metal salt such as sodium salt, potassium salt and the like; alkaline earth metal salt such as magnesium salt, calcium salt and the like; ammonium salt such as ammonium salt, alkylammonium salt, etc. and the like can be mentioned. The salt of synthetic intermediate for compound (1) is the same as the salt of compound (1).

Now, preferable embodiments of the production methods of the compounds of the present invention are explained. The compound of the present invention can be produced by various methods, and can be produced by the following Scheme I.

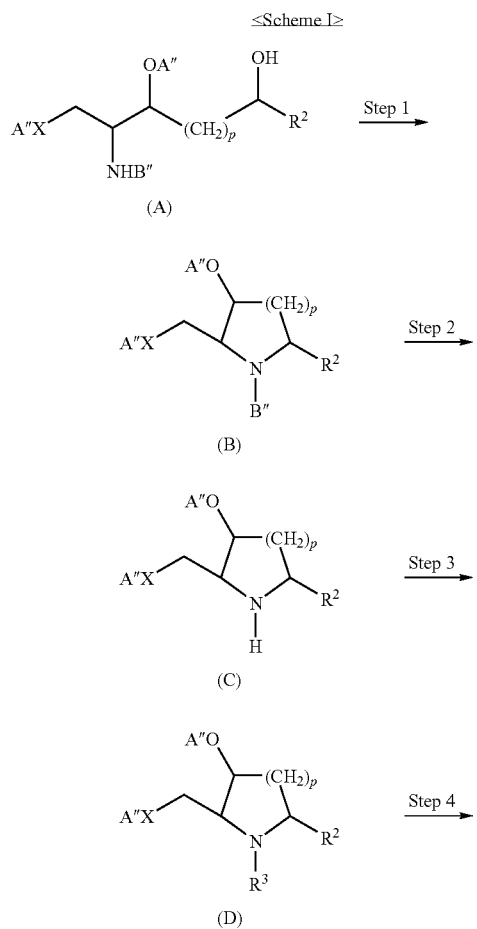

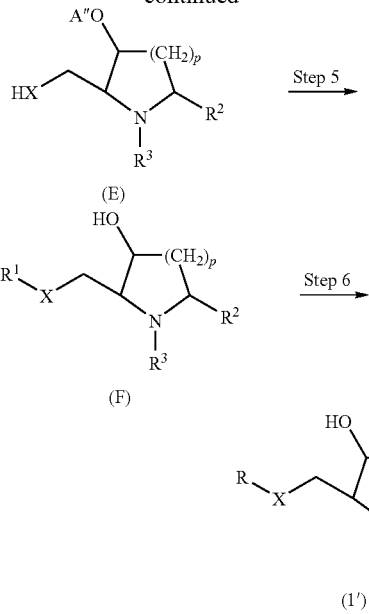

Each step is explained in detail in the following.
(Step 1)

In Step 1, compound (A) is intramolecularly-cyclized to give compound (B). Specifically, a sulfonylating agent is added to compound (A) in the presence of a base to sulfonylate the hydroxyl group of compound (A), and then the sulfonyloxy group is removed to allow cyclization. As the sulfonylating agent, methanesulfonyl chloride, p-toluenesulfonyl chloride and the like are preferable. As the base, pyridine, triethylamine, diisopropylethylamine and the like can be mentioned, with preference given to pyridine. The amount of the base to be used is generally 1-20 equivalents, preferably 1-10 equivalents, relative to compound (A). The amount of the sulfonylating agent to be used is generally 1.5-10 equivalents, preferably 2-8 equivalents, relative to compound (A). The reaction temperature is generally $-20°$ C. to room temperature, preferably 0-4° C., and the reaction time is generally 12-72 hr, preferably 18-48 hr. In addition, the above-mentioned reaction can be performed in the presence of a solvent as necessary, and any solvent can be used as long as it does not inhibit the reaction. As the solvent, for example, halogen solvent (e.g., dichloromethane, chloroform) can be mentioned. After completion of the reaction, the reaction solution was diluted with water and extracted with solvent such as diethyl ether and the like. The obtained organic layer is washed with aqueous saturated copper sulfate solution, water, saturated brine and the like and dried over anhydrous magnesium sulfate and the like.

Then, the obtained crude product is dissolved in a solvent, and the sulfonyl group is removed in the presence of a base to allow cyclization. As the base, sodium hydride, potassium tert-butoxide and the like can be mentioned. The amount of the base to be used is generally 2-6 equivalents, preferably 3-4 equivalents, relative to compound (A). The reaction temperature is generally 0-60° C., preferably room temperature, and the reaction time is generally 12-72 hr, preferably 24-48 hr. As the solvent, any solvent can be used as long as it does not inhibit the reaction and, for example, ether solvent can be mentioned. Tetrahydrofuran is particularly preferable. The amount of the solvent to be used is generally 5- to 50-fold volume, preferably 10- to 20-fold volume, relative to the crude product. After completion of the reaction, the reaction solution is diluted with water and saturated aqueous ammonium chloride solution and extracted with solvent such as diethyl ether and the like. The obtained organic layer is washed with saturated brine and the like, dried over anhydrous magnesium sulfate and the like, and filtrated. The filtrate is concentrated under reduced pressure, and the residue is purified by column chromatography to give compound (B) in a high yield. In addition, compound (A) can be obtained using aldehyde and alkyne as starting materials, which are subjected to a coupling reaction, followed by several steps.
(Step 2)

In Step 2, an N atom-protecting group (B") in cyclic amine of compound (B) is removed to give compound (C). This step is generally performed in a solvent. While the removal method varies depending on the protecting group, for example, in the case of a tosyl group, a reducing agent is added to a solution of compound (B) to allow reaction. As the reducing agent, for example, an organic metal reagent such as sodium naphthalenide and the like can be mentioned. The amount of the reducing agent to be used is generally 5-50 equivalents, preferably 8-20 equivalents, relative to compound (B). The reaction temperature is generally −78° C. to −20° C., preferably −78° C. to −60° C., and the reaction time is generally 1-4 hr, preferably 1-2 hr. As the solvent, for example, ether solvent can be mentioned, and 1,2-dimethoxyethane is particularly preferable. The amount of the solvent to be used is generally 5- to 50-fold volume, preferably 10- to 20-fold volume, relative to compound (B). After completion of the reaction, the reaction solution is diluted with water, and extracted with a solvent such as chloroform and the like. The obtained organic layer is washed with saturated brine and the like, dried over anhydrous magnesium sulfate and the like, and filtrated. The filtrate is concentrated under reduced pressure, and the residue is purified by column chromatography to give compound (C) in a high yield.
(Step 3)

In Step 3, an N atom in cyclic amine of compound (C) is acylated to give compound (D). This step is performed in a solvent. For example, a base, a condensation agent and a fatty acid are added to a solution of compound (C) to allow reaction. As the fatty acid, C2-28 fatty acid is generally used, which may be saturated or unsaturated. Particularly, higher fatty acid is preferable, and C16-28 saturated fatty acid is more preferable. Specifically, palmitic acid, stearic acid, cerotic acid and the like can be mentioned and, of these, cerotic acid is particularly preferable. As the base, the aforementioned bases can be recited as examples, with preference given to diisopropylethylamine. As the condensation agent, a conventionally known condensation agent can be used and, for example, carbodiimides such as 1,3-diisopropylcarbodiimide (DIC), 1-ethyl-3-(3-dimethylaminopropyl)carbodiimide (EDC) hydrochloride, N,N'-dicyclohexylcarbodiimide (DCC) and the like can be mentioned, and EDC hydrochloride is more preferable. The amount of the base to be used is generally 1-20 equivalents, preferably 1-10 equivalents, relative to compound (C). The amount of the condensation agent to be used is generally 1-6 equivalents, preferably 1-2 equivalents, relative to compound (C). The amount of the fatty acid to be used is generally 1-6 equivalents, preferably 1-2 equivalents, relative to compound (C). In addition, a catalytic amount of 4-(dimethylamino)pyridine and the like may be added as necessary. The reaction temperature is generally 0° C. to a temperature for heating under reflux, preferably room temperature, and the reaction time is generally 24-96 hr, preferably 48-72 hr. As the solvent, for example, halogen solvent can be mentioned, and dichloromethane is particularly preferable. The amount of the solvent to be used is generally 5- to 50-fold volume, preferably 10- to 20-fold volume, relative to compound (C). After completion of the reaction, the reaction solution is diluted with water, and extracted with a solvent such as diethyl ether and the like. The obtained organic layer is washed with saturated brine and the like, dried over anhydrous magnesium sulfate and the like, and filtrated. The filtrate is concentrated under reduced pressure, and the residue is purified by column chromatography to give compound (D) in a high yield. In addition, compound (C) may be reacted with a reactive derivative such as acid halide (e.g., acid chloride and the like), acid anhydride, mixed acid anhydride and the like in the presence of a base.
(Step 4)

In Step 4, the —XH-protecting group (A") of —$CH_2$XH at the 2-position of cyclic amine of compound (D) is selectively removed to give compound (E). This step is generally performed in a solvent. While the removal method varies depending on the protecting group, in the case of TBS group, for example, an acid such as trifluoromethanesulfonic acid, p-toluenesulfonic acid, acetic acid, trifluoroacetic acid, hydrochloric acid, strong acid ion exchange resin and the like is added to a solution of compound (D) to allow reaction. The amount of the acid to be used is generally a catalytic amount to 10-fold volume, preferably 1- to 2-fold volume, relative to compound (D). The reaction temperature is generally −20° C.—room temperature, preferably room temperature, and the reaction time is generally 2-12 hr, preferably 2-4 hr. As the solvent, for example, ether solvent can be mentioned, and tetrahydrofuran is particularly preferable. The amount of the solvent to be used is generally 5- to 100-fold volume, preferably 10- to 50-fold volume, relative to compound (D). After completion of the reaction, the reaction solution is neutralized with a basic aqueous solution such as aqueous sodium hydroxide solution and the like, and extracted with a solvent such as diethyl ether and the like. The obtained organic layer is washed with saturated aqueous sodium hydrogencarbonate solution, saturated brine and the like, dried over anhydrous magnesium sulfate and the like, and filtrated. The filtrate is concentrated under reduced pressure, and the residue is purified by column chromatography to give compound (E) in a high yield.
(Step 5)

In Step 5, compound (E) is derivatized into adldopyranosyl and a hydroxyl-protecting group (A") at the 3-position of cyclic amine is removed to give compound (F). This step is generally performed in a solvent. While the conditions for derivatization into aldopyranosyl vary depending on the kind of saccharide donor, aldopyranosyl halide ($R^1$—$X^1$, $X^1$ is halogen) wherein a hydroxyl group is protected is added to a solution of compound (E) in the presence of an activator, a Lewis acid and a dehydrating agent to allow reaction. As the activator, for example, tin chloride can be mentioned. As the Lewis acid, for example, silver perchlorate can be mentioned. Moreover, as the dehydrating agent, molecular sieves and the like can be mentioned. The amount of the activator to be used is generally 2-4 equivalents, preferably 3-4 equivalents, relative to compound (E). The amount of the Lewis acid to be used is generally 2-4 equivalents, preferably 3-4 equivalents, relative to compound (E). The amount of the dehydrating agent to be used is generally 2- to 4-fold weight, preferably 3- to 4-fold weight, relative to compound (E). As the aldopyranosyl halide wherein a hydroxyl group is protected, one wherein hydroxyl group at the 2, 3, 4 or 6-position is protected with benzyl(Bn) group is preferable. As the halogen, fluorine atom is preferable. The amount of the aldopyranosyl halide to be used wherein hydroxyl group is protected is generally 2-4 equivalents, preferably 2-3 equivalents, relative to compound (E). The reaction temperature is generally −20° C. to room temperature, and the reaction time is generally 2-12 hr, preferably 2-4 hr. As the solvent, for example, ether solvent can be mentioned, and tetrahydrofuran is particularly preferable. The amount of the solvent to be used is generally 10- to 100-fold volume, preferably 20- to 50-fold volume, relative to compound (E). After completion of the reaction, the reaction solution is filtered through silica gel and the like. The filtrate is washed with saturated brine and the like, dried over anhydrous magnesium sulfate and the like, and filtrated. The filtrate is concentrated under reduced pressure, and the residue is purified by column chromatography to give two fractions (less polar fraction and high polar fraction).

Then, the obtained two fractions (less polar fraction and high polar fraction) are each dissolved in an ether solvent such as tetrahydrofuran and the like. A desilylation agent (e.g., tetrabutylammonium fluoride) is added to this solution and the mixture is stirred at room temperature for about 12-48 hr. After completion of the reaction, the reaction solution is diluted with water, and extracted with diethyl ether and the like. The obtained organic layer is washed with saturated brine and the like, dried over anhydrous magnesium sulfate and the like, and filtrated. The filtrate is concentrated under reduced pressure, and the residue is purified by column chromatography to give compound (F) wherein a hydroxyl group at the 2, 3, 4 or 6-position of an aldopyranose residue is protected. While compound (F) contains an α form and a β form, they are separated into two fractions (e.g., less polar fraction, high polar fraction), and each fraction is subjected to this operation to efficiently separate and purify the α form and β form. Alternatively, α form and β form of compound (F) may be separated and purified using solvents with different polarity during column chromatography.

(Step 6)

In Step 6, a hydroxyl-protecting group of aldopyranose of compound (F) is removed to give compound (1'). This step is generally performed in a solvent. While the removal method varies depending on the protecting group, in the case of a Bn group, for example, compound (F) is reacted in the presence of hydrogen and a reduction catalyst. The reaction is performed generally at room temperature for about 12-24 hr. As the reduction catalyst, palladium hydroxide-carbon catalyst, palladium oxide, Raney-nickel and the like can be used. As the amount of the reduction catalyst to be used, a general catalytic amount relative to compound (F) is sufficient. As the solvent, a mixed solvent of an alcohol solvent and a halogen solvent is preferable, and a mixed solvent of ethanol and chloroform is more preferable. The amount of the solvent to be used is generally 10- to 200-fold volume, preferably 50- to 150-fold volume, relative to compound (F). After completion of the reaction, the reaction solution is filtered through Celite and the like, and washed with the aforementioned solvent. The filtrate is concentrated under reduced pressure, and the residue is purified by column chromatography to give compound (1'), the object glycolipid, in a high yield. The α form and β form of compound (1') may be separated and purified using solvents with different polarity during column chromatography. In addition, the α form and β form of compound (1') can be obtained using, as a starting material, α form or β form of compound (F) isolated in Step 5.

Particularly, as the production method of the compound of the present invention, the method described in Scheme 1 is preferable.

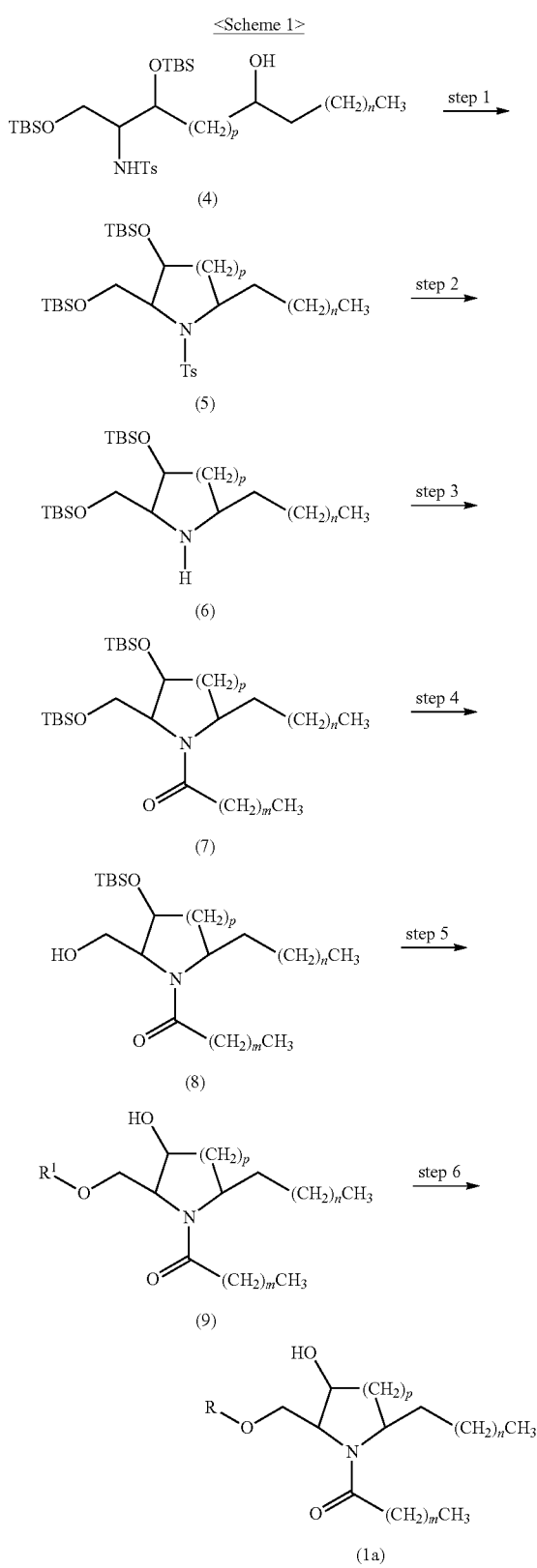

In Scheme II described below, shown is the step for obtaining compound (H) by ring opening of the epoxy group of compound (G).

<Scheme II>

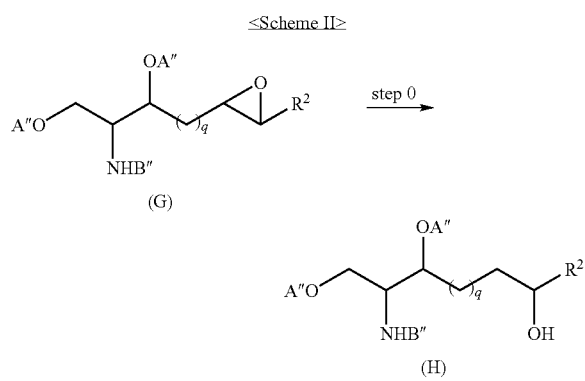

This step is performed in a solvent, and a reducing agent is added to a solution of compound (G) to allow reaction. As the reducing agent, for example, aluminum hydride compounds such as diisobutylaluminum hydride, lithium aluminum hydride and the like, and borohydride compounds such as sodium borohydride, potassium borohydride and the like can be mentioned. The amount of the reducing agent to be used is generally 4-12 equivalents, preferably 4-8 equivalents, relative to compound (G). The reaction temperature is generally −78° C. to 0° C., and the reaction time is generally 3-6 hr. As the solvent, ether solvent is preferable, and tetrahydrofuran is particularly preferable. When a halogen solvent or a hydrocarbon solvent is used, the above-mentioned reaction hardly proceeds. However, using tetrahydrofuran reaction can be specifically carried out. The amount of the solvent to be used is generally 5- to 50-fold volume, preferably 10- to 20-fold volume, relative to compound (G). After completion of the reaction, saturated aqueous potassium sodium tartrate solution and the like are added to the reaction solution, and the mixture is diluted with a solvent such as diethyl ether and the like, stirred and extracted with diethyl ether. The obtained organic layer is washed with saturated brine and the like, dried over anhydrous magnesium sulfate and the like, and filtrated. The filtrate is concentrated under reduced pressure, and the residue is purified by column chromatography to give compound (H) in a high yield. The epoxy compound (G) can be produced according to the description in Tetrahedron 1998, 54, 3141.

As a preferable production method, among others, the method described in Scheme 2 can be mentioned.

<Scheme 2>

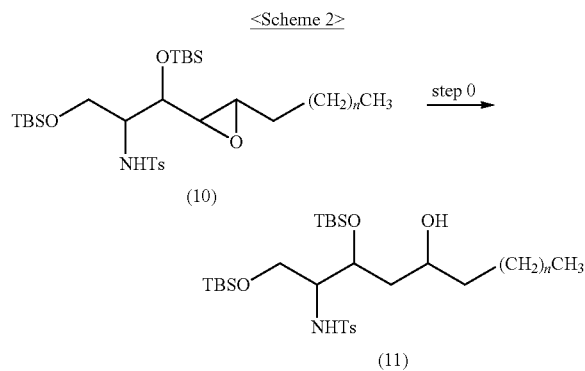

Now, the agent for the prophylaxis or treatment of an autoimmune disease, NKT cell activator, selective IL-4 production inducing agent and agent for the prophylaxis or treatment of a disease caused by hyperfunction of Th1 cell of the present invention are explained.

Administration of compound (1') or compound (1) (hereinafter to be abbreviated as the compound of the present invention) activates NKT cell to selectively induce IL-4 production alone and, unlike α-galactosylceramide, strikingly reduces IFN-γ production. Therefore, an autoimmune disease can be prevented or treated without aggravating the condition. In addition, while the Th1/Th2 immunity balance deviates toward Th1 during the episode of autoimmune diseases, the Th1/Th2 immunity balance can be corrected by the administration of the compound of the present invention. Therefore, the prophylaxis or treatment of a disease caused by hyperfunction of Th1 cell is made possible. While an α form or a β form alone or in a mixture thereof can be used as the compound of the present invention, an α form is preferable from the aspect of pharmacological effect.

As the autoimmune diseases treatable by the compound of the present invention, multiple sclerosis, rheumatoid arthritis, psoriasis, Crohn's disease, vitiligo vulgaris, Behcet's disease, collagen disease, Type I diabetes mellitus, uveitis, Sjogren's syndrome, autoimmune myocarditis, autoimmune hepatic diseases, autoimmune gastritis, pemphigus, Guillain-Barre syndrome, HTLV-1-associated myelopathy and the like in mammals (e.g., mouse, feline, bovine, canine, equine, goat, monkey, human) can be mentioned. In addition, as the disease caused by hyperfunction of Th1 cell, multiple sclerosis, rheumatoid arthritis, psoriasis, Type I diabetes mellitus, uveitis, Sjogren's syndrome, fulminant hepatitis, transplant rejection, infection with intracellular contagium and the like in mammals can be mentioned.

When the compound of the present invention is administered to human, the compound per se or as a pharmaceutical composition obtained by admixing the compound with a pharmacologically acceptable carrier, excipient, diluent and the like, such as an agent for oral administration (e.g., powder, granule, tablet, capsule), an agent for parenteral administration (e.g., injection), suppository (e.g., rectal suppository, vaginal suppository) and the like, can be safely administered orally or parenterally. These preparations can be produced by a conventionally known method.

As the injection, subcutaneous injection, intravenous injection, intramuscular injection, intraperitoneal injection, drip infusion and the like can be mentioned. The injection can also be provided as an aqueous injection by processing the compound of the present invention with a solubilizer (e.g., β-cyclodextrins), dispersing agent (e.g., carboxymethylcellulose, sodium alginate), preservative (e.g., methylparaben, propylparaben, benzyl alcohol, chlorobutanol), isotonicity agent (e.g., sodium chloride, glycerol, sorbitol, glucose) and the like according to a conventional method. In addition, the compound may be dissolved, suspended or emulsified in vegetable oil (e.g., olive oil, sesame oil, peanut oil, cottonseed oil, corn oil), propylene glycol and the like to give an oily injection.

The agent for oral administration can also be produced by appropriately adding, for example, excipient (e.g., lactose, sucrose, starch), disintegrant (e.g., starch, calcium carbonate), binder (e.g., starch, gum arabic, carboxymethylcellulose, polyvinylpyrrolidone, hydroxypropylcellulose) or lubricant (e.g., talc, magnesium stearate, polyethylene glycol) and the like to the compound of the present invention, compressing the mixture into a form, and coating the form with hydroxypropylmethylcellulose and the like as necessary. The suppository can be produced by mixing the compound of the present invention and a nonirritating excipient (e.g., polyethylene glycol, glyceride of higher fatty acid).

While the dose of the compound of the present invention varies depending on the age, body weight, symptom, dosage form, administration method, dosing period and the like, for example, 0.1-1 mg/kg, preferably 0.5-1 mg/kg, more preferably 0.8-1 mg/kg, is generally administered orally or parenterally per day to one patient (adult, body weight about 60 kg) in one to several portions.

EXAMPLES

The present invention is explained more specifically in the following by referring to the following Examples, which are not to be construed as limitative.

Example 1

Synthesis of a Compound Represented by the Following Formula (16)

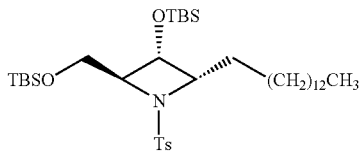
(16)

To a solution of the following compound 17 (460 mg, 0.657 mmol) in absolute pyridine (5.0 ml) was added methanesulfonyl chloride (0.20 ml, 2.58 mmol) under ice-cooling, and the mixture was stirred at 4° C. for 18 hr. The reaction solution was diluted with water and extracted with diethyl ether. The combined organic layer was washed with saturated aqueous copper sulfate solution, water and saturated brine and dried over anhydrous magnesium sulfate. After filtration, the filtrate was concentrated under reduced pressure to give a mesylated crude product. The mesylated crude product was dissolved in absolute tetrahydrofuran (5.0 ml), and under ice-cooling, 60% sodium hydride (79.0 mg, 1.98 mmol) was added, and the mixture was stirred at room temperature for 40 hr. The reaction solution was diluted with water and saturated aqueous ammonium chloride solution, and extracted with diethyl ether. The combined organic layer was washed with saturated brine and dried over anhydrous magnesium sulfate. After filtration, the filtrate was concentrated under reduced pressure, and the residue was purified by silica gel column chromatography (25 g, hexane-ethyl acetate, 60:1-30:1) to give compound 16 (360 mg, 80%).

$^1$H NMR (500 MHz, CDCl$_3$) δ 0.01 (3H, s), 0.02 (3H, s), 0.03 (3H, s), 0.04 (3H, s), 0.84 (9H, s), 0.87 (9H, s), 0.88 (3H, t, J=7.1 Hz), 1.21-1.31 (24H, m), 1.74-1.79 (2H, m), 2.41 (3H, s), 3.80 (1H, dd, J=3.2, 11.2 Hz), 3.85 (1H, dd, J=4.9, 11.2 Hz), 3.97 (1H, m), 4.22 (1H, m), 4.41 (1H, dd, J=3.2, 6.6 Hz), 7.26 (2H, d, J=8.5 Hz), 7.71 (2H, d, J=8.3 Hz)

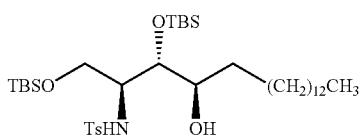
(17)

Example 2

Synthesis of a Compound Represented by the Following Formula (18)

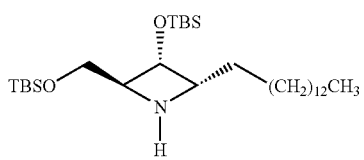
(18)

(1) Preparation of Sodium Naphthalenide
Under an argon atmosphere, to a solution of naphthalene (516 mg, 4.03 mmol) in absolute 1,2-dimethoxyethane (5.0 ml) was added sodium (77.4 mg, 3.37 mmol), and the mixture was stirred at room temperature for 3 hr.

(2) Detosylation
Under an argon atmosphere, to a solution of compound 16 (286 mg, 0.419 mmol) in absolute 1,2-dimethoxyethane (3.0 ml) was added dropwise prepared sodium naphthalenide (5.0 ml) at −78° C. The reaction solution was stirred for 90 min, diluted with water, and extracted with chloroform. The combined organic layer was washed with saturated brine and dried over anhydrous sodium sulfate. After filtration, the filtrate was concentrated under reduced pressure, and the residue was purified by silica gel column chromatography (15 g, chloroform-methanol, 1:0-20:1) to give compound 18 (221 mg, 100%).

$^1$H NMR (500 MHz, CDCl$_3$) δ 0.02 (3H, s), 0.02 (3H, s), 0.06 (3H, s), 0.07 (3H, s), 0.87 (3H, t, J=7.1 Hz), 0.88 (9H, s), 0.91 (9H, s), 1.25-1.38 (24H, m), 1.57-1.72 (2H, m), 2.14 (1H, brs), 3.55 (1H, m), 3.61 (1H, m), 3.66 (2H, d, J=4.2 Hz), 4.43 (1H, dd, J=5.6, 7.3 Hz)

Example 3

Synthesis of a Compound Represented by the Following Formula (19)

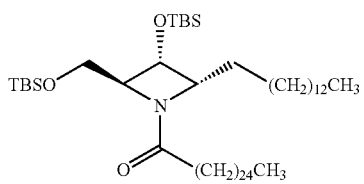
(19)

To a solution of compound 18 (129 mg, 0.244 mmol) in absolute dichloromethane (10.0 ml) were added diisopropylethylamine (0.30 ml, 1.72 mmol), cerotic acid (148 mg, 0.373 mmol), 1-ethyl-3-(3-dimethylaminopropyl)-carbodiimide hydrochloride (71.0 mg, 0.370 mmol) and a catalytic amount of 4-(dimethylamino)pyridine, and the mixture was stirred at room temperature for 62 hr. The reaction solution was diluted with water and extracted with diethyl ether. The combined organic layer was washed with saturated brine and dried over anhydrous magnesium sulfate. After filtration, the filtrate was concentrated under reduced pressure, and the residue was purified by silica gel column chromatography (5 g, hexane-ethyl acetate, 50:1-30:1) to give compound 19 (159 mg, 72%).

¹H NMR (500 MHz, CDCl₃) δ 0.02-0.07 (12H, m), 0.86-0.91 (6H, m), 0.88 (9H, s), 0.89 (9H, s), 1.25-1.31 (68H, m), 1.56-2.11 (6H, m), 3.67 (0.75H, dd, J=2.0, 11.0 Hz), 3.76 (0.25H, dd, J=3.2, 11.2 Hz), 3.84 (0.25H, dd, J=4.2, 11.2 Hz), 4.01 (0.25H, m), 4.04 (0.75H, m), 4.18 (0.75H, m), 4.23 (0.25H, m), 4.29 (0.75H, dd, J=2.9, 11.0 Hz), 4.35 (0.25H, dd, J=3.2, 6.6 Hz), 4.58 (0.75H, dd, J=3.7, 6.8 Hz)

Example 4

Synthesis of a Compound Represented by the Following Formula (20)

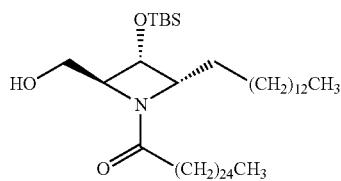

(20)

To a solution of compound 19 (64.2 mg, 70.8 μmol) in absolute tetrahydrofuran (3.0 ml) was added trifluoromethanesulfonic acid (10% aqueous solution, 1.0 ml) under ice-cooling, and the mixture was stirred at room temperature for 3 hr. The reaction solution was neutralized with aqueous sodium hydroxide solution and extracted with diethyl ether. The combined organic layer was washed with saturated aqueous sodium hydrogencarbonate solution and saturated brine and dried over anhydrous magnesium sulfate. After filtration, the filtrate was concentrated under reduced pressure, and the residue was purified by silica gel column chromatography (5 g, hexane-ethyl acetate, 50:1-4:1) to give compound 20 (55.7 mg, 99%).

¹H NMR (500 MHz, CDCl₃) δ 0.04 (3H, s), 0.06 (3H, s), 0.86-0.91 (6H, m), 0.89 (9H, s), 1.19-1.36 (68H, m), 1.61-1.65 (3H, m), 1.99 (1H, m), 2.09 (2H, t, J=7.6 Hz), 3.65 (1H, dd, J=9.5, 11.0 Hz), 3.80 (1H, ddd, J=2.0, 11.0, 11.7 Hz), 4.17 (1H, dd, J=5.6, 7.3 Hz), 4.28 (2H, m), 5.42 (1H, d, J=9.8 Hz)

Example 5

Synthesis of Compounds Represented by the Following Formulas (21) and (22)

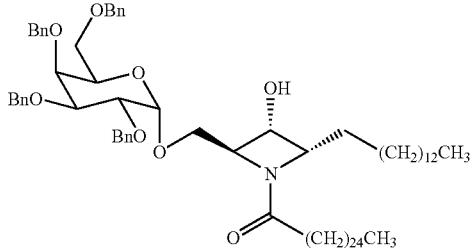

(21)

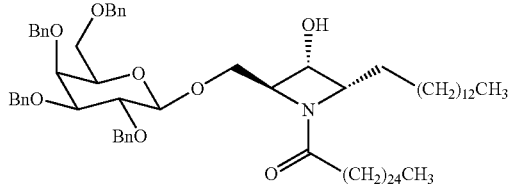

(22)

To a solution of compound 20 (127 mg, 0.160 mmol) in absolute tetrahydrofuran (5.0 ml) were added tin chloride (91.8 mg, 0.485 mmol), silver perchlorate (99.8 mg, 0.481 mmol) and molecular sieves 4A (300 mg), and the mixture was stirred at room temperature for 90 min. After stirring, benzyl sugar fluoride (210 mg, 0.387 mmol) was added at −20° C. and the mixture was stirred and gradually warmed to 10° C. over 4 hr. The reaction solution was filtered through silica gel, and the filtrate was washed with water and saturated brine and dried over anhydrous magnesium sulfate. After filtration, the filtrate was concentrated under reduced pressure, and the residue was roughly separated by silica gel column chromatography (20 g, hexane-ethyl acetate, 1:0-6:1) to give two fractions (146 mg of less polar fraction and 122 mg of high polar fraction).

The obtained less polar fraction (146 mg) was dissolved in tetrahydrofuran (5.0 ml), tetrabutylammonium fluoride (1.0 M tetrahydrofuran solution, 0.75 ml, 0.75 mmol) was added, and the mixture was stirred at room temperature for 15 hr. The reaction solution was diluted with water and extracted with diethyl ether. The combined organic layer was washed with saturated brine and dried over anhydrous magnesium sulfate. After filtration, the filtrate was concentrated under reduced pressure, and the residue was purified by silica gel column chromatography (20 g, hexane-ethyl acetate, 10:1-3:2) to give compound 21 (82.8 mg, 2 steps 43%).

¹H NMR (500 MHz, CDCl₃) δ 0.87-0.89 (6H, m), 1.13-2.06 (74H, m), 3.28 (0.33H, dd, J=3.9, 9.8 Hz), 3.39 (0.67H, dd, J=5.4, 9.8 Hz), 3.55 (1H, dd, J=7.1, 9.8 Hz), 3.60 (0.33H, dd, J=8.1, 11.0 Hz), 3.67 (0.67H, dd, J=8.3, 11.0 Hz), 3.83 (0.33H, m), 3.87-3.90 (1.67H, m), 3.96 (0.67H, m), 3.99-4.06 (1.67H, m), 4.10-4.22 (2H, m), 4.33-4.41 (2.67H, m), 4.46 (0.33H, d, J=11.7 Hz), 4.47 (0.67H, d, J=11.7 Hz), 4.54 (0.33H, d, J=11.5 Hz), 4.55 (0.67H, d, J=11.5 Hz), 4.64 (0.33H, d, J=12.0 Hz), 4.65 (0.67H, d, J=12.0 Hz), 4.73 (0.67H, d, J=11.7 Hz), 4.73 (0.33H, d, J=11.7 Hz), 4.77 (0.33H, d, J=3.7 Hz), 4.79 (0.67H, d, J=12.0 Hz), 4.82 (0.67H, d, J=3.7 Hz), 4.83 (0.67H, d, J=11.7 Hz), 4.83 (0.33H, d, J=11.7 Hz), 4.87 (0.33H, d, J=12.0 Hz), 4.92 (0.67H, d, J=11.5 Hz), 4.93 (0.33H, d, J=11.5 Hz), 7.23-7.40 (20H, m)

The obtained high polar fraction (122 mg) was dissolved in tetrahydrofuran (5.0 ml), tetrabutylammonium fluoride (1.0 M tetrahydrofuran solution, 0.75 ml, 0.75 mmol) was added, and the mixture was stirred at room temperature for 15 hr. The reaction solution was diluted with water and extracted with diethyl ether. The combined organic layer was washed with saturated brine and dried over anhydrous magnesium sulfate. After filtration, the filtrate was concentrated under reduced pressure, and the residue was purified by silica gel column chromatography (20 g, hexane-ethyl acetate, 10:1-3:2) to give compound 22 (93.4 mg, 2 steps 49%).

¹H NMR (500 MHz, CDCl₃) δ 0.88 (6H, t, J=7.1 Hz), 1.13-2.41 (74H, m), 3.46-3.60 (4.33H, m), 3.71 (0.33H, dd, J=6.3, 11.0 Hz), 3.77-3.85 (2H, m), 4.06 (0.67H, dd, J=5.9, 11.2 Hz), 4.10-4.25 (3H, m), 4.35 (0.33H, d, J=6.8 Hz), 4.36 (0.67H, d, J=7.8 Hz), 4.39 (0.67H, d, J=12.0 Hz), 4.40 (0.33H, d, J=12.0 Hz), 4.46 (1H, d, J=11.7 Hz), 4.58-4.63 (1.67H, m), 4.67-4.78 (3H, m), 4.83 (0.33H, d, J=11.2 Hz), 4.86 (0.67H, d, J=11.2 Hz), 4.91 (0.67H, d, J=11.5 Hz), 4.93 (0.33H, d, J=11.5 Hz), 7.24-7.37 (20H, m)

Example 6

Synthesis of a Compound Represented by the Following Formula (23)

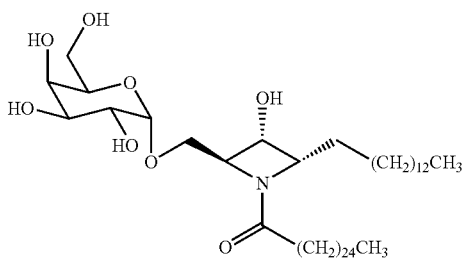

(23)

Under an argon atmosphere, to a mixed solution of compound 21 (44.2 mg, 36.8 μmol) in ethanol (3.0 ml) and chloroform (1.0 ml) was added 20% palladium hydroxide-carbon catalyst (5 mg), and the mixture was vigorously stirred at room temperature for 20 hr under a hydrogen atmosphere. The reaction solution was filtered through Celite and washed with chloroform and methanol. The filtrate was concentrated under reduced pressure, and the residue was purified by silica gel column chromatography (3 g, chloroform-methanol, 20:1-10:1) to give compound 23 (12.7 mg, 41%).

$^1$H NMR (500 MHz, pyridine-d) δ 0.83-0.86 (6H, m), 1.14-2.60 (74H, m), 4.01 (0.40H, dd, J=3.7, 11.0 Hz), 4.13 (0.60H, dd, J=2.7, 10.3 Hz), 4.33-4.72 (8.40H, m), 4.81 (0.60H, dd, J 4.6, 10.3 Hz), 5.06-5.20 (1H, m), 5.40 (0.60H, J=3.7 Hz), 5.44 (0.40H, d, J=3.7 Hz)

Example 7

Synthesis of a Compound Represented by the Following Formula (24)

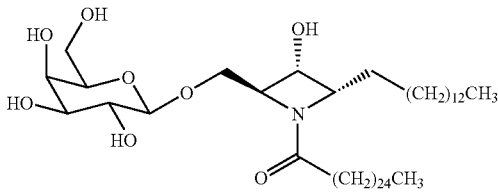

(24)

Under an argon atmosphere, to a mixed solution of compound 22 (41.8 mg, 34.8 μmol) in ethanol (3.0 ml) and chloroform (1.0 ml) was added 20% palladium hydroxide-carbon catalyst (5 mg), and the mixture was vigorously stirred at room temperature for 20 hr under a hydrogen atmosphere. The reaction solution was filtered through Celite and washed with chloroform and methanol. The filtrate was concentrated under reduced pressure, and the residue was purified by silica gel column chromatography (3 g, chloroform-methanol, 20:1-10:1) to give compound 24 (5.1 mg, 17%).

$^1$H NMR (500 MHz, CDCl$_3$-CD$_3$OD) δ 0.89 (6H, t, J=6.8 Hz), 1.16-1.43 (64H, m), 1.54-1.67 (3.25H, m), 1.87 (0.25H, d, J=14.2 Hz), 1.96 (0.75H, d, J=13.7 Hz), 2.03-2.45 (3.75H, m), 3.31-4.33 (9H, m), 4.08 (0.25 H, dd, J=3.9, 10.5 Hz), 4.11 (0.75H, dd, J=3.7, 10.5 Hz), 4.22 (0.25H, d, J=7.6 Hz), 4.24 (0.75H, d, J=7.6 Hz), 4.46 (0.75H, d, J=4.9 Hz), 4.47 (0.25H, d, J=4.9 Hz)

$^1$H NMR (500 MHz, pyridine-d) δ 0.83-0.86 (6H, m), 1.13-2.59 (74H, m), 4.02 (0.60H, m), 4.07-4.19 (2H, m), 4.40-4.50 (3.20H, m), 4.54-4.61 (2.60H, m), 4.68 (0.60H, m), 4.71 (0.60H, d, J=11.0 Hz), 4.72 (0.40H, d, J=10.7 Hz), 4.88 (0.40H, d, J=7.8 Hz), 4.88 (0.60H, d, J=7.8 Hz), 4.95 (0.40H, dd, J=3.7, 6.8 Hz), 5.11 (0.60H, dd, J=4.2, 6.8 Hz)

Example 8

Synthesis of a Compound Represented by the Following Formula (25)

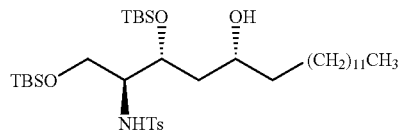

(25)

Under an argon atmosphere, to a solution of compound 26 (540 mg, 0.773 mmol) in absolute tetrahydrofuran (10.0 ml) was added dropwise diisobutylaluminum hydride (0.95M hexane solution, 4.2 ml, 3.99 mmol) at −78° C., and the mixture was gradually warmed to 0° C. over 3 hr. To the reaction solution was added saturated aqueous potassium sodium tartrate solution and diluted with diethyl ether. The mixture was stirred at room temperature for 2 hr and extracted with diethyl ether. The combined organic layer was washed with saturated brine and dried over anhydrous magnesium sulfate. After filtration, the filtrate was concentrated under reduced pressure, and the residue was purified by silica gel column chromatography (25 g, hexane-ethyl acetate, 30:1-15:1) to give compound 25 (462 mg, 85%).

$^1$H NMR (500 MHz, CDCl$_3$) δ −0.07 (3H, s), −0.03 (3H, s), −0.01 (3H, s), 0.01 (3H, s), 0.83 (9H, s), 0.85 (9H, s), 0.88 (3H, t, J=7.0 Hz), 1.21-1.40 (24H, m), 1.67-1.76 (2H, m), 2.37 (1H, d, J=5.4 Hz), 2.41 (3H, s), 3.32 (1H, dd, J=6.1, 10.3 Hz), 3.49 (1H, m), 3.71 (1H, dd, J=4.4, 10.3 Hz), 3.80 (1H, m), 4.07 (1H, dd, J=5.1, 11.5 Hz), 5.05 (1H, d, J=7.1 Hz), 7.29 (2H, d, J=8.1 Hz), 7.74 (2H, d, J=8.1 Hz)

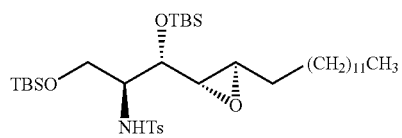

(26)

Example 9

Synthesis of a Compound Represented by the Following Formula (27)

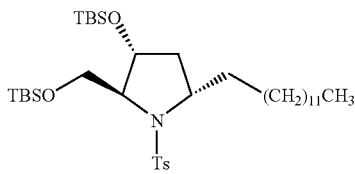

(27)

To a solution of compound 25 (1.024 g, 1.46 mmol) in absolute pyridine (10.0 ml) was added methanesulfonyl chloride (904 μl, 11.7 mmol) under ice-cooling, and the mixture was stirred at 4° C. for 42 hr. The reaction solution was diluted with water and extracted with diethyl ether. The combined organic layer was washed with saturated aqueous copper sulfate solution, water and saturated brine and dried over anhydrous magnesium sulfate. After filtration, the filtrate was concentrated under reduced pressure to give a mesylated crude product. The mesylated crude product was dissolved in absolute tetrahydrofuran (10.0 ml), under ice-cooling, 60% sodium hydride (180 mg, 4.50 mmol) was added, and the mixture was stirred at room temperature for 40 hr. The reaction solution was diluted with water and extracted with diethyl ether. The combined organic layer was washed with saturated brine and dried over anhydrous magnesium sulfate. After filtration, the filtrate was concentrated under reduced pressure, and the residue was purified by silica gel column chromatography (25 g, hexane-ethyl acetate, 30:1-20:1) to give compound 27 (973 mg, 97%).

$^1$H NMR (500 MHz, CDCl$_3$) δ 0.02 (3H, s), 0.03 (3H, s), 0.06 (3H, s), 0.06 (3H, s), 0.79 (9H, s), 0.88 (3H, t, J=7.0 Hz), 0.89 (9H, s), 1.12-1.33 (22H, m), 1.49-1.59 (1H, m), 1.76 (1H, d, J=13.4 Hz), 1.89 (1H, m), 2.14 (1H, ddd, J=4.4, 9.0, 13.4 Hz), 2.39 (3H, s), 3.36 (1H, dd, J=9.3, 10.3 Hz), 3.73 (1H, dd, J=3.9, 9.0 Hz), 3.90 (1H, ddd, J=3.4, 9.0, 14.0 Hz), 4.04 (1H, dd, J=3.9, 10.3 Hz), 4.39 (1H, d, J=4.2 Hz), 7.22 (2H, d, J=7.8 Hz), 7.77 (2H, d, J=7.8 Hz)

Example 10

Synthesis of a Compound Represented by the Following Formula (28)

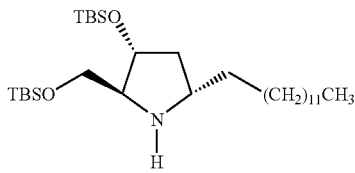

(28)

(1) Preparation of Sodium Naphthalenide

Under an argon atmosphere, to a solution of naphthalene (1.86 g, 14.5 mmol) in absolute 1,2-dimethoxyethane (12.0 ml) was added sodium (267 mg, 11.6 mmol), and the mixture was stirred at room temperature for 3 hr.

(2) Detosylation

Under an argon atmosphere, to a solution of compound 27 (484 mg, 0.693 mmol) in absolute 1,2-dimethoxyethane (3.0 ml) was added dropwise the prepared sodium naphthalenide (6.0 ml) at −78° C. The reaction solution was stirred for 90 min, diluted with water and extracted with chloroform. The combined organic layer was washed with saturated brine and dried over anhydrous sodium sulfate. After filtration, the filtrate was concentrated under reduced pressure, and the residue was purified by silica gel column chromatography (25 g, chloroform-methanol, 1:0-20:1) to give compound 28 (349 mg, 93%).

$^1$H NMR (500 MHz, CDCl$_3$) δ 0.05 (6H, s), 0.05 (6H, s), 0.87 (3H, t, J=6.8 Hz), 0.87 (9H, s), 0.89 (9H, s), 1.25-1.55 (22H, m), 1.39 (1H, ddd, J=6.8, 7.6, 12.5 Hz), 2.01 (1H, brs), 2.13 (1H, ddd, J=6.8, 6.9, 12.7 Hz), 2.95 (1H, ddd, J=4.6, 4.9, 9.8 Hz), 3.08 (1H, dddd, J=7.1, 7.1, 7.1, 7.1 Hz), 3.59 (2H, d, J=4.6 Hz), 4.09 (1H, ddd, J=5.4, 6.6, 6.6 Hz)

Example 11

Synthesis of a Compound Represented by the Following Formula (29)

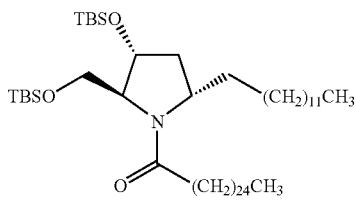

(29)

To a solution of compound 28 (132 mg, 0.250 mmol) in absolute dichloromethane (10.0 ml) were added diisopropylethylamine (0.30 ml, 1.72 mmol), cerotic acid (150 mg, 0.378 mmol), 1-ethyl-3-(3-dimethylaminopropyl)-carbodiimide hydrochloride (75.0 mg, 0.391 mmol) and a catalytic amount of 4-(dimethylamino)pyridine, and the mixture was stirred at room temperature for 42 hr. The reaction solution was diluted with water and extracted with diethyl ether. The combined organic layer was washed with saturated brine and dried over anhydrous magnesium sulfate. After filtration, the filtrate was concentrated under reduced pressure, and the residue was purified by silica gel column chromatography (20 g, hexane-ethyl acetate, 20:1-10:1) to give compound 29 (175 mg, 77%).

$^1$H NMR (500 MHz, CDCl$_3$) δ 0.02 (2H, s), 0.03 (2H, s), 0.04 (1H, s), 0.05 (1H, s), 0.06 (2H, s), 0.07 (2H, s), 0.08 (1H, s), 0.09 (1H, s), 0.84-0.92 (6H, m), 0.86 (6H, s), 0.87 (6H, s), 0.88 (3H, s), 0.89 (3H, s), 1.25-1.30 (66H, m), 1.56-1.67 (3H, m), 1.76 (0.33H, d, J=13.9 Hz), 1.81 (0.67H, d, J=13.2 Hz), 1.99-2.34 (4H, m), 3.18 (0.33H, dd, J=10.0, 10.3 Hz), 3.53 (0.67H, dd, J=6.6, 10.0 Hz), 3.56 (0.33H, dd, J=3.9, 10.3 Hz), 3.70-3.74 (1H, m), 3.83 (0.67H, dd, J=3.2, 10.0 Hz), 3.94 (0.33H, m), 4.02 (0.67H, dd, J=2.9, 6.6 Hz), 4.33 (0.67H, d, J=4.6 Hz), 4.38 (0.33H, d, J=4.2 Hz)

Example 12

Synthesis of a Compound Represented by the Following Formula (30)

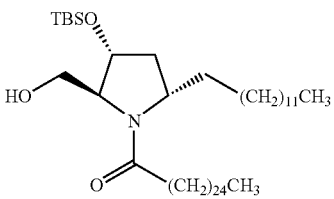

(30)

To a solution of compound 29 (86.2 mg, 95.1 μmol) in absolute tetrahydrofuran (3.0 ml) was added trifluoromethanesulfonic acid (10% aqueous solution, 1.0 ml) under ice-cooling, and the mixture was stirred at room temperature for 3 hr. The reaction solution was neutralized with aqueous sodium hydroxide solution and extracted with diethyl ether. The combined organic layer was washed with saturated aqueous sodium hydrogencarbonate solution and saturated brine and dried over anhydrous magnesium sulfate. After filtration, the filtrate was concentrated under reduced pressure, and the residue was purified by silica gel column chromatography (5 g, hexane-ethyl acetate, 50:1-4:1) to give compound 30 (69.0 mg, 92%).

$^1$H NMR (500 MHz, CDCl$_3$) δ 0.07 (3H, s), 0.08 (3H, s), 0.86-0.89 (6H, m), 0.88 (9H, s), 1.13-1.31 (66H, m), 1.60-1.69 (3H, m), 1.83 (1H, d, J=13.2 Hz), 2.01-2.09 (2H, m), 2.31 (2H, t, J=7.7 Hz), 3.59 (1H, dd, J=7.1, 11.0 Hz), 3.70 (1H, m), 3.82 (1H, m), 4.06-4.09 (2H, m), 4.47 (1H, m)

Example 13

Synthesis of Compounds Represented by the Following Formulas (31) and (32)

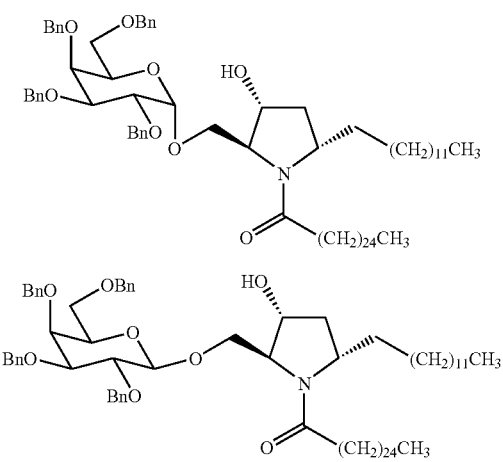

To a solution of compound 30 (114 mg, 0.114 mmol) in absolute tetrahydrofuran (5.0 ml) were added tin chloride (82.4 mg, 0.435 mmol), silver perchlorate (90.1 mg, 0.435 mmol) and molecular sieves 4Å (300 mg), and the mixture was stirred at room temperature for 90 min. Benzyl sugar fluoride (189 mg, 0.348 mmol) was added at −20° C. and the mixture was stirred and gradually warmed to room temperature over 2 hr. The reaction solution was filtered through silica gel, and the filtrate was washed with saturated brine and dried over anhydrous magnesium sulfate. After filtration, the filtrate was concentrated under reduced pressure, and the residue was roughly separated by silica gel column chromatography (20 g, hexane-ethyl acetate, 10:1-6:1) to give two fractions (142 mg of less polar fraction and 93 mg of high polar fraction).

The obtained less polar fraction (142 mg) was dissolved in tetrahydrofuran (4.0 ml), tetrabutylammonium fluoride (1.0 M tetrahydrofuran solution, 0.50 ml, 0.50 mmol) was added, and the mixture was stirred at room temperature for 45 hr. The reaction solution was diluted with water and extracted with diethyl ether. The combined organic layer was washed with saturated brine and dried over anhydrous magnesium sulfate. After filtration, the filtrate was concentrated under reduced pressure, and the residue was purified by silica gel column chromatography (10 g, hexane-ethyl acetate, 10:1-3:1) to give compound 31 (84.4 mg, 2 steps 49%).

$^1$H NMR (500 MHz, CDCl$_3$) δ 0.87 (6H, m), 1.21-1.37 (66H, m), 1.58-1.63 (3H, m), 1.69 (0.33H, d, J=13.9 Hz), 1.79 (0.67H, d, J=13.7 Hz), 1.88 (0.67H, m), 2.02-2.30 (3.33H, m), 3.28-3.34 (1.33H, m), 3.42-3.54 (2H, m), 3.62 (0.67H, m), 3.81-3.94 (4.33H, m), 4.03 (0.67H, dd, J=3.7, 10.0 Hz), 4.04 (0.33H, dd, J=3.7, 9.8 Hz), 4.12 (0.67H, m), 4.31 (0.67H, m), 4.35 (0.33H, m), 4.36 (0.33H, d, J=11.7 Hz), 4.37 (0.67H, d, J=11.7 Hz), 4.46 (1H, d, J=11.7 Hz), 4.56 (0.67H, d, J=11.5 Hz), 4.56 (0.33H, d, J=11.5 Hz), 4.62 (0.33H, d, J=12.0 Hz), 4.66 (0.67H, d, J=11.5 Hz), 4.72 (0.33H, d, J=11.7 Hz), 4.73 (0.67H, d, J=11.7 Hz), 4.74 (0.33H, d, J=3.7 Hz), 4.78 (0.67H, d, J=11.7 Hz), 4.79 (0.67H, d, J=12.0 Hz), 4.82 (0.33H, d, J=12.2 Hz), 4.85 (0.33H, d, J=12.0 Hz), 4.87 (0.67H, d, J=3.7 Hz), 4.92 (0.67H, d, J=11.5 Hz), 4.93 (0.33H, d, J=11.5 Hz), 7.22-7.40 (20H, m)

The obtained high polar fraction (93 mg) was dissolved in tetrahydrofuran (4.0 ml), tetrabutylammonium fluoride (1.0M tetrahydrofuran solution, 0.50 ml, 0.50 mmol) was added, and the mixture was stirred at room temperature for 45 hr. The reaction solution was diluted with water and extracted with diethyl ether. The combined organic layer was washed with saturated brine and dried over anhydrous magnesium sulfate. After filtration, the filtrate was concentrated under reduced pressure, and the residue was purified by silica gel column chromatography (10 g, hexane-ethyl acetate, 8:1-3:1) to give compound 32 (32.0 mg, 2 steps 19%).

$^1$H NMR (500 MHz, CDCl$_3$) δ 0.86-0.89 (6H, m), 1.13-1.34 (66H, m), 1.47-1.62 (3H, m), 1.79 (0.33H, d, J=13.7 Hz), 1.88 (0.67H, d, J=13.7 Hz), 1.94 (0.67H, m), 2.04-2.35 (3.33H, m), 3.20 (0.33H, dd, J=10.3, 11.0 Hz), 3.29 (0.67H, dd, J=4.9, 9.8 Hz), 3.39-3.45 (1H, m), 3.48-3.53 (1.33H, m), 3.55-3.60 (1H, m), 3.64-3.69 (1.67H, m), 3.74-3.85 (2.33H, m), 3.91-3.98 (0.67H, m), 4.22-4.25 (1.33H, m), 4.28 (0.33H, d, J=7.8 Hz), 4.36 (0.67H, d, J=11.7 Hz), 4.38 (0.33H, d, J=12.0 Hz), 4.41 (0.67H, d, J=7.8 Hz), 4.45 (0.33H, d, J=11.0 Hz), 4.47 (0.67H, d, J=11.7 Hz), 4.54 (0.67H, d, J=5.4 Hz), 4.58 (0.67H, d, J=11.7 Hz), 4.60 (0.33H, d, J=10.5 Hz), 4.68 (0.67H, d, J=11.7 Hz), 4.71 (0.33H, d, J=11.7 Hz), 4.74 (0.67H, d, J=11.5 Hz), 4.75 (0.33H, d, J=11.7 Hz), 4.76 (0.67H, d, J=11.2 Hz), 4.81 (0.67H, s), 4.82 (0.67H, d, J=11.2 Hz), 4.91 (0.67H, d, J=12.0 Hz), 4.93 (0.33H, d, J=11.7 Hz), 7.24-7.34 (20H, m)

Example 14

Synthesis of a Compound Represented by the Following Formula (33)

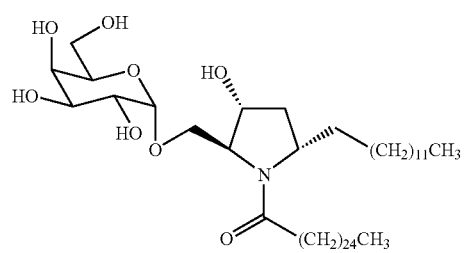

Under an argon atmosphere, to a mixed solution of compound 31 (39.8 mg, 33.1 μmol) in ethanol (3.0 ml) and chloroform (1.0 ml) was added 20% palladium hydroxide-carbon catalyst (5 mg), and the mixture was vigorously stirred at room temperature for 15 hr under a hydrogen atmosphere. The reaction solution was filtered through Celite and washed with chloroform and methanol. The filtrate was concentrated under reduced pressure, and the residue was purified by silica gel column chromatography (3 g, chloroform-methanol, 12:1-8:1) to give compound 33 (26.5 mg, 95%).

$^1$H NMR (500 MHz, CDCl$_3$-CD$_3$OD) δ 0.88 (6H, t, J=6.8 Hz), 1.15-1.38 (66H, m), 1.53-1.64 (2H, m), 1.84 (0.25H, d, J=13.9 Hz), 1.97 (0.75H, d, J=13.9 Hz), 2.00-2.40 (3H, m), 3.29 (0.75H, dd, J=9.5, 9.5 Hz), 3.52 (0.25H, m), 3.63-3.98 (8.25H, m), 4.10 (0.75H, dd, J=2.7, 8.8 Hz), 4.33 (0.75H, d, J=4.9 Hz), 4.40 (0.25H, d, J=4.6 Hz) 4.84 (0.25H, d, J=3.9 Hz), 4.92 (0.75H, d, J=3.9 Hz)

$^1$H NMR (500 MHz, pyridine-d) δ 0.83-0.87 (6H, m), 1.14-1.45 (64H, m), 1.76-1.95 (2.5H, m), 2.10 (0.5H, d, J=13.4 Hz), 2.13-2.22 (0.5H, m), 2.20 (0.5H, d, J=13.4 Hz), 2.45-2.64 (3.5H, m), 2.67-2.72 (0.5H, m), 3.75 (0.5H, dd, J=3.4, 10.3 Hz), 3.91-3.97 (1H, m), 4.06-4.11 (1H, m), 4.25 (0.5H, dd, J=3.2, 9.3 Hz), 4.31-4.49 (4.5H, m), 4.57 (0.5H, dd, J=2.9, 9.0 Hz), 4.57 (1H, d, J=2.9 Hz), 4.67 (0.5H, dd, J=3.9, 10.0 Hz), 4.72 (0.5H, dd, J=3.9, 10.0 Hz), 4.96 (0.5H, dd, J=2.7, 7.8 Hz), 5.00 (0.5H, dd, J=4.9, 4.9 Hz), 5.40 (0.5H, d, J=3.9 Hz), 5.43 (0.5H, d, J=3.7 Hz)

Example 15

Synthesis of a Compound Represented by the Following Formula (34)

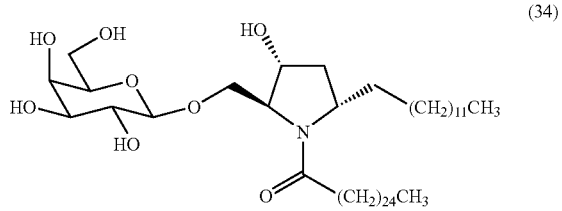

(34)

Under an argon atmosphere, to a mixed solution of compound 32 (30.6 mg, 25.5 μmol) in ethanol (3.0 ml) and chloroform (1.0 ml) was added 20% palladium hydroxide-carbon catalyst (5 mg), and the mixture was vigorously stirred at room temperature for 15 hr under a hydrogen atmosphere. The reaction solution was filtered through Celite and washed with chloroform and methanol. The filtrate was concentrated under reduced pressure, and the residue was purified by silica gel column chromatography (2 g, chloroform-methanol, 10:1-6:1) to give compound 34 (13.6 mg, 64%).

$^1$H NMR (500 MHz, CDCl$_3$-CD$_3$OD) δ 0.89 (6H, t, J=6.8 Hz), 1.16-1.43 (64H, m), 1.54-1.67 (3.25H, m), 1.87 (0.25H, d, J=14.2 Hz), 1.96 (0.75H, d, J=13.7 Hz), 2.03-2.45 (3.75H, m), 3.31-4.33 (9H, m), 4.08 (0.25 H, dd, J=3.9, 10.5 Hz), 4.11 (0.75H, dd, J=3.7, 10.5 Hz), 4.22 (0.25H, d, J=7.6 Hz), 4.24 (0.75H, d, J=7.6 Hz), 4.46 (0.75H, d, J=4.9 Hz), 4.47 (0.25H, d, J=4.9 Hz)

Experimental Example 1

The spleen cells removed from the spleen of mouse were individually prepared to 2×10$^5$ cells/well (96-well plate) using RPMI1640 culture medium (manufactured by Sigma Corporation) containing 10% fetal calf serum (FCS). A reagent was added to the culture medium at each of the concentrations of 2 ng/mL, 20 ng/mL and 200 ng/mL. The cytokine amount in the culture supernatant 4 days later was measured by sandwich ELISA assay. As the test substances, compounds 33 and 34 obtained in Examples 14 and 15 were used, and α-galactosylceramide represented by the following formula (a) (α-GC, abbreviated as compound a in the Figure) was used as a control substance. In addition, DMSO was used as a control.

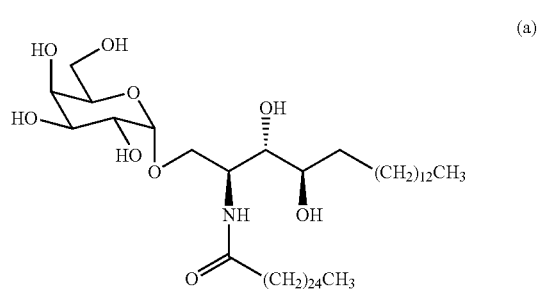

(a)

Figure 2:
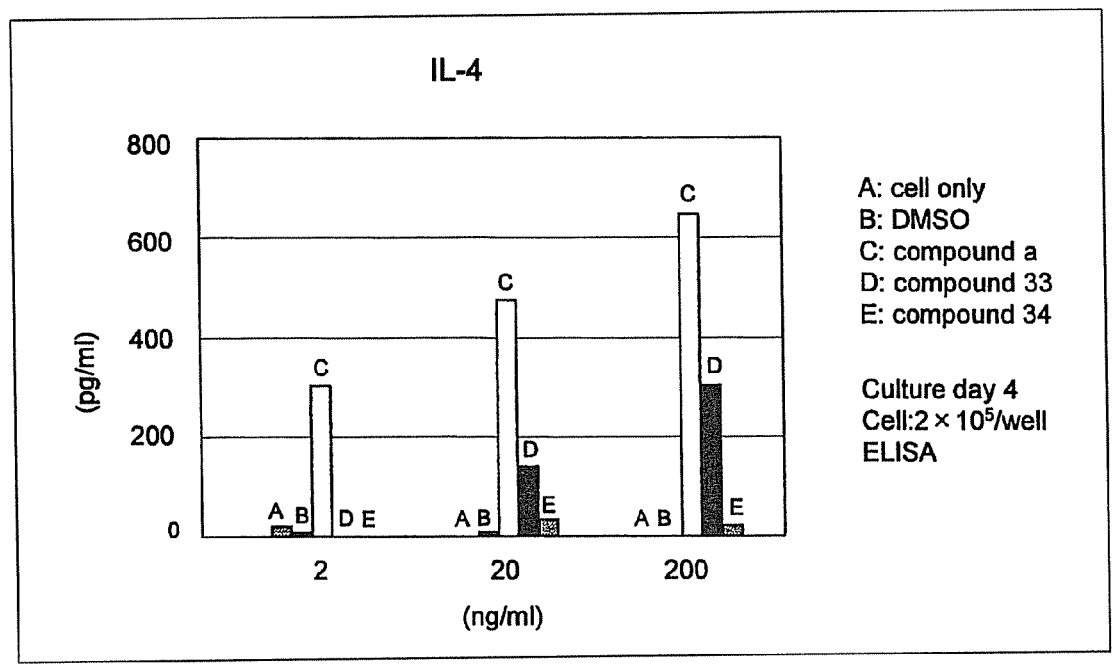
FIG. 2 shows the measurement results of the IL-4 production amount by sandwich ELISA assay in Experimental Example 1.

The measurement results of IFN-γ are shown in FIG. 1 and the measurement results of IL-4 are shown in FIG. 2. In the Figure, A shows the measurement results of cell alone, B shows the measurement results when DMSO was used, C shows the measurement results when α-GC was used, D shows the measurement results when compound 33 was used, and E shows the measurement results when compound 34 was used. From these results, α-galactosylceramide produced both IFN-γ and IL-4 in large amounts, while compounds 33 and 34 obtained in Examples (particularly, compound 33) showed a IL-4 preferential cytokine production pattern.

Experimental Example 2

Figure 3:
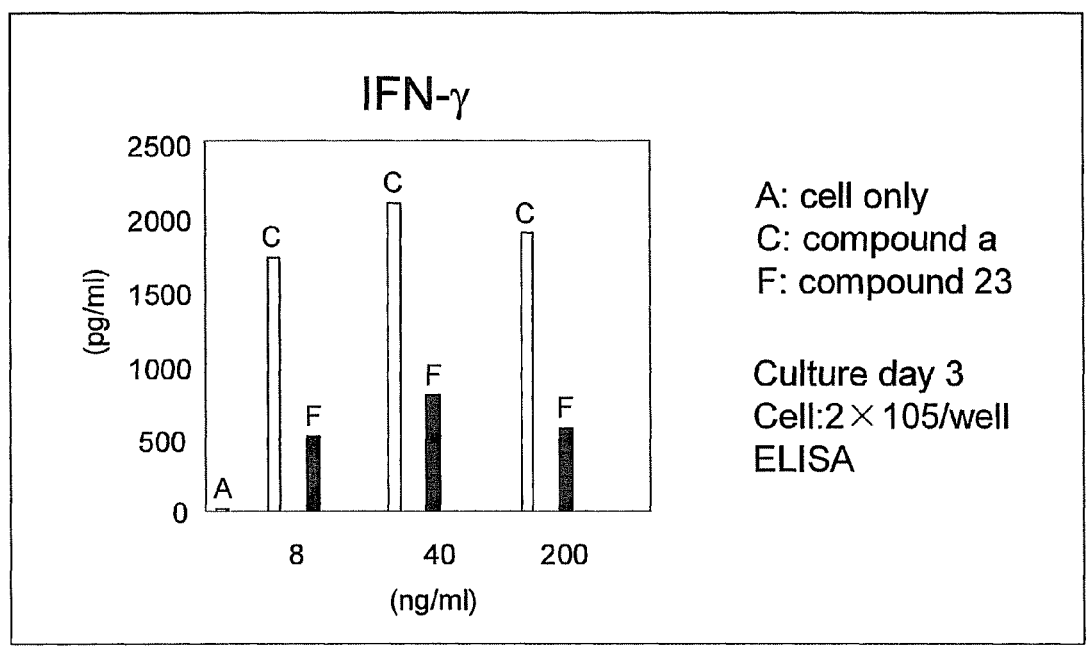
FIG. 3 shows the measurement results of the IFN-γ production amount by sandwich ELISA assay in Experimental Example 2.
Figure 4:
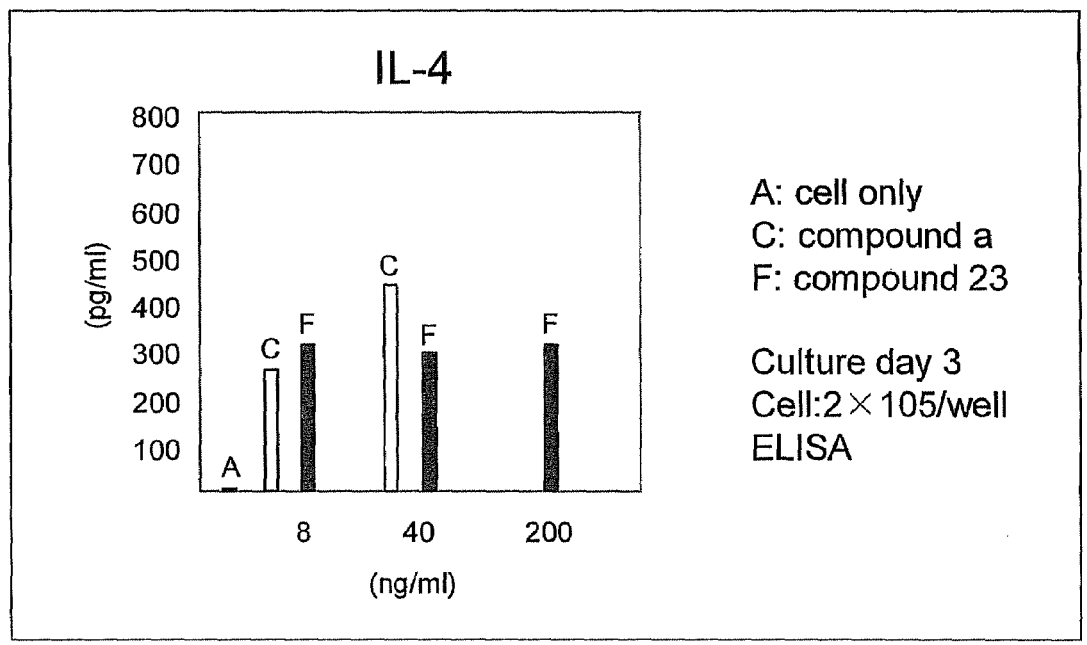
FIG. 4 shows the measurement results of the IL-4 production amount by sandwich ELISA assay in Experimental Example 2.
Figure 5:
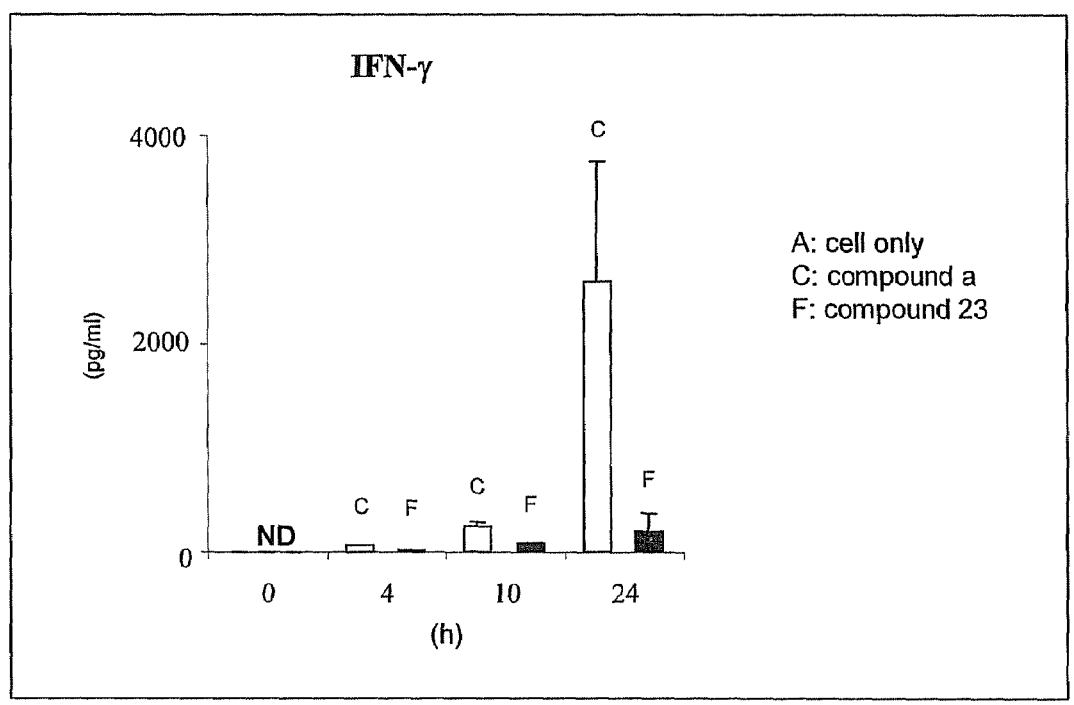
FIG. 5 shows time course changes in the IFN-γ production amount in Experimental Example 2.
Figure 6:
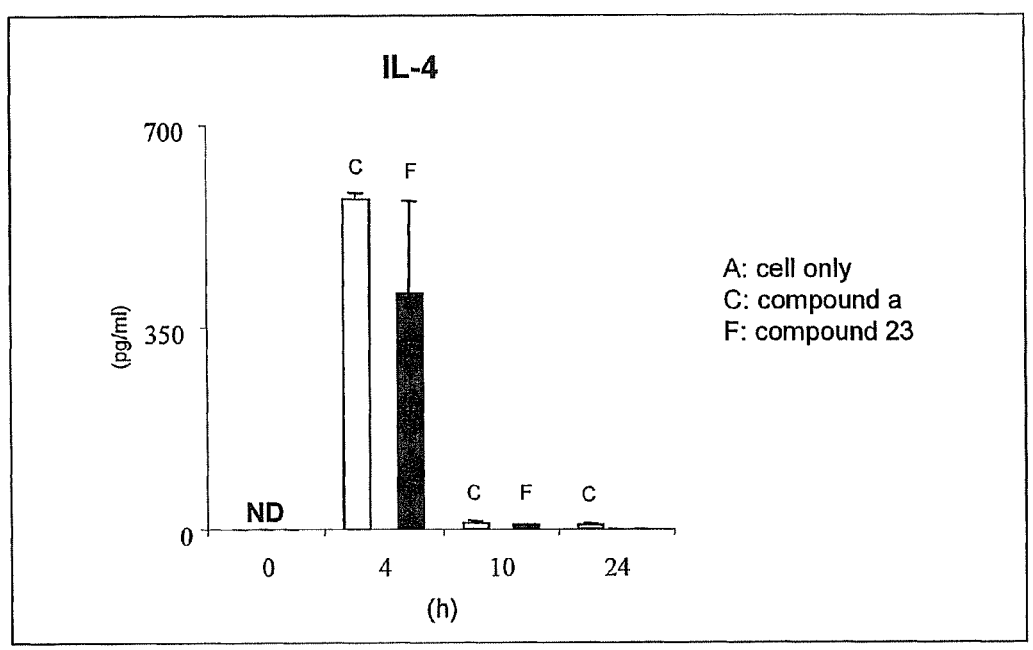
FIG. 6 shows time course changes in the IL-4 production amount in Experimental Example 2.

The cytokine amount was measured by sandwich ELISA assay in the same manner as in Experimental Example 1 except that compound 23 obtained in Example 6 was used as a test substance. The measurement results of IFN-γ are shown in FIG. 3 and the measurement results of IL-4 are shown in FIG. 4. In addition, the time course changes in the amount of IFN-γ production are shown in FIG. 5, and the time course changes in the amount of IL-4 production are shown in FIG. 6. In the Figures, A shows the measurement results of cell alone, C shows the measurement results when α-GC was used, and F shows the measurement results when compound 23 was used. From these results, it was confirmed that compound 23 also has an ability to preferentially induce IL-4 production.

From the foregoing, it has been confirmed that the compound of the present invention is effective as a therapeutic drug for the pathology ameliorated by IL-4, for example, a therapeutic drug for autoimmune diseases.

Industrial Applicability

According to the present invention, a compound having a cyclic structure, which is effective for the prophylaxis or treatment of an autoimmune disease, an intermediate useful for synthesis of the compound, and production methods thereof can be provided.

A pharmaceutical agent comprising the compound of the present invention as an active ingredient on administration activates NKT cell and selectively induces IL-4 production alone. Thus, it is free of side effects to be particularly noted and enables prophylaxis or treatment of autoimmune diseases and prophylaxis or treatment of diseases caused by hyperfunction of Th1 cell. In addition, the compound of the present invention can also be used as a reagent for biological experiments and researches.

This application is based on application No. 2005-059934 filed in Japan, the contents of which are entirely incorporated hereinto by reference.

The invention claimed is:

1. A compound represented by the following formula (1') or a salt thereof:

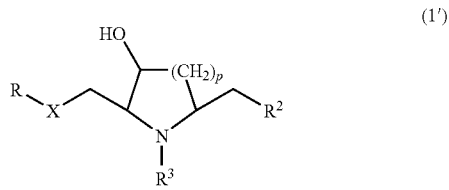

wherein R is an aldopyranose residue, $R^2$ is a C2-18 hydrocarbon group optionally having substituent(s), $R^3$ is an acyl group, X is an oxygen atom, a sulfur atom or —NH—, and p is an integer of 0-4.

2. The compound of claim 1, which is represented by the following formula (1) or a salt thereof:

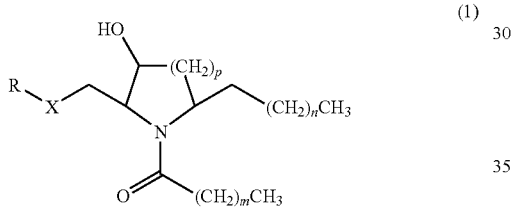

wherein R is an aldopyranose residue, X is an oxygen atom, a sulfur atom or —NH—, m is an integer of 0-26, n is an integer of 0-16 and p is an integer of 0-4.

3. The compound of claim 1, wherein R is α-D-galactopyranosyl, or a salt thereof.

4. A compound represented by the following formula (3) or a salt thereof:

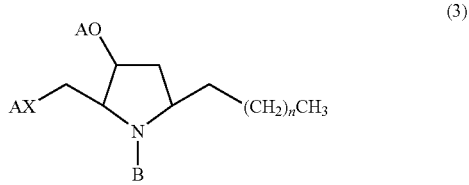

wherein
X is an oxygen atom, a sulfur atom or —NH—,
each A is independently a hydrogen atom or a t-butyldimethylsilyl group,
B is a hydrogen atom, a tosyl group or —CO(CH$_2$)$_m$CH$_3$ (m is an integer of 0-26) and
n is an integer of 0-16.

5. A pharmaceutical composition comprising (a) the compound of claim 1, or a salt thereof and (b) a pharmaceutically acceptable carrier.

6. A method of therapeutically treating an autoimmune disease in a mammal in need thereof, comprising administering to the mammal an effective amount of the compound of claim 1, or a salt thereof, whereupon the disease is therapeutically treated.

7. A method of activating an NKT cell in a mammal in need thereof, comprising administering to the mammal an effective amount of the compound of claim 1, or a salt thereof, whereupon the NKT cell is activated.

8. A method of selectively inducing IL-4 production in a mammal in need thereof, comprising administering to the mammal an effective amount of the compound of claim 1, or a salt thereof, whereupon IL-4 production is selectively induced.

9. The compound of claim 2, wherein R is α-D-galactopyranosyl, or a salt thereof.

10. The pharmaceutical composition of claim 5, wherein the compound is represented by the following formula (1) or a salt thereof:

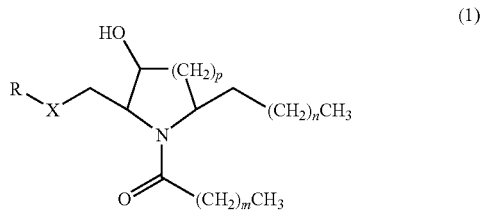

wherein R is an aldopyranose residue, X is an oxygen atom, a sulfur atom or —NH—, m is an integer of 0-26, n is an integer of 0-16 and p is an integer of 0-4.

11. The pharmaceutical composition of claim 5, wherein R is α-D-galactopyranosyl, or a salt thereof.

12. The method of claim 6, wherein the autoimmune disease is selected from the group consisting of multiple sclerosis, rheumatoid arthritis, psoriasis, Crohn's disease, vitiligo vulgaris, Behcet's disease, collagen disease, Type I diabetes mellitus, uveitis, Sjogren's syndrome, autoimmune myocarditis, autoimmune hepatic diseases, autoimmune gastritis, pemphigus, Guillain-Barre syndrome, and HTLV-1-associated myelopathy.

13. The method of claim 6, wherein the compound is represented by the following formula (1) or a salt thereof:

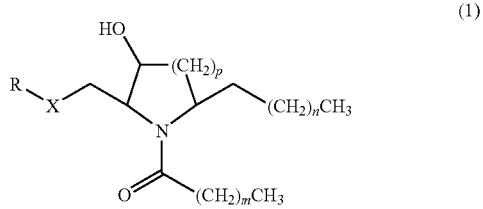

wherein R is an aldopyranose residue, X is an oxygen atom, a sulfur atom or —NH—, m is an integer of 0-26, n is an integer of 0-16 and p is an integer of 0-4.

14. The method of claim 6, wherein R is α-D-galactopyranosyl, or a salt thereof.

15. The method of claim 7, wherein the compound is represented by the following formula (1) or a salt thereof:

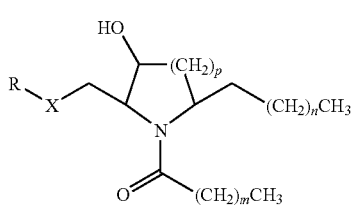

(1)

wherein R is an aldopyranose residue, X is an oxygen atom, a sulfur atom or —NH—, m is an integer of 0-26, n is an integer of 0-16 and p is an integer of 0-4.

16. The method of claim 7, wherein R is α-D-galactopyranosyl, or a salt thereof.

17. The method of claim 8, wherein the compound is represented by the following formula (1) or a salt thereof:

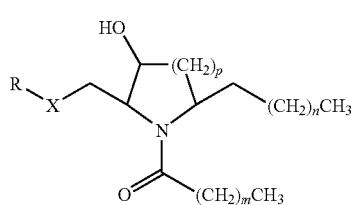

(1)

wherein R is an aldopyranose residue, X is an oxygen atom, a sulfur atom or —NH—, m is an integer of 0-26, n is an integer of 0-16 and p is an integer of 0-4.

18. The method of claim 8, wherein R is α-D-galactopyranosyl, or a salt thereof.

* * * * *